United States Patent
Webler

(10) Patent No.: US 8,983,582 B2
(45) Date of Patent: Mar. 17, 2015

(54) METHODS AND APPARATUSES FOR POSITIONING WITHIN AN INTERNAL CHANNEL

(75) Inventor: William E. Webler, Escondido, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 1913 days.

(21) Appl. No.: 11/018,634

(22) Filed: Dec. 20, 2004

(65) Prior Publication Data

US 2006/0135870 A1 Jun. 22, 2006

(51) Int. Cl.
*A61B 6/00* (2006.01)
*A61B 1/00* (2006.01)
(Continued)

(52) U.S. Cl.
CPC ............ *A61B 5/6852* (2013.01); *A61B 1/00183* (2013.01); *A61B 1/0051* (2013.01); *A61B 1/00096* (2013.01); *A61B 1/3137* (2013.01); *A61B 2019/5234* (2013.01);
(Continued)

(58) Field of Classification Search
CPC ............ A61B 5/6852; A61B 1/00183; A61B 1/0051; A61B 1/00096; A61B 1/3137; A61B 2019/5234; A61B 2017/22081; A61B 5/0062; A61B 5/0066; A61B 5/0084; A61B 5/01; A61B 5/02007; A61B 5/6853; A61B 5/6885; A61B 8/12
USPC ............................. 606/171; 600/473, 478, 476
See application file for complete search history.

(56) References Cited

U.S. PATENT DOCUMENTS 4,169,464 A * 10/1979 Obrez ........................ 600/434
4,601,283 A    7/1986 Chikama
(Continued)

FOREIGN PATENT DOCUMENTS

EP    0963764 A1    12/1999
EP    1013301 A1    6/2000
(Continued)

OTHER PUBLICATIONS

JG Fujimoto, et al. "High resolution in vivo intra-arterial imaging with optical coherence tomography." Heart 1999; 82:128-133.
(Continued)

*Primary Examiner* — Long V. Le
*Assistant Examiner* — Helene Bor
(74) *Attorney, Agent, or Firm* — Randy Shen; Blakely Sokoloff Taylor & Zafman LLP

(57) ABSTRACT

Methods and apparatuses for positioning medical devices onto (or close to) a desired portion of the interior wall of an internal channel, such as for scan imaging, for photodynamic therapy and/or for optical temperature measurement. In one embodiment, a catheter assembly has a distal portion that can be changed from a configuration suitable for traversing the internal channel to another configuration suitable for scan at least a spiral section of the interior wall of an internal channel, such as an artery. In one example, the distal portion spirals into gentle contact with (or close to) a spiral section of the artery wall for Optical Coherence Tomography (OCT) scanning. The spiral radius may be changed through the use of a guidewire, a tendon, a spiral balloon, a tube, or other ways.

7 Claims, 20 Drawing Sheets

(51) Int. Cl.
*A61B 5/00* (2006.01)
*A61B 1/005* (2006.01)
*A61B 1/313* (2006.01)
*A61B 5/01* (2006.01)
*A61B 5/02* (2006.01)
*A61B 19/00* (2006.01)
*A61B 17/22* (2006.01)
*A61B 8/12* (2006.01)

(52) U.S. Cl.
CPC .... *A61B 2017/22081* (2013.01); *A61B 5/0062* (2013.01); *A61B 5/0066* (2013.01); *A61B 5/0084* (2013.01); *A61B 5/01* (2013.01); *A61B 5/02007* (2013.01); *A61B 5/6853* (2013.01); *A61B 5/6885* (2013.01); *A61B 8/12* (2013.01)
USPC ........... 600/478; 600/467; 600/476; 606/171; 606/108; 604/530

(56) References Cited

U.S. PATENT DOCUMENTS

| | | | |
|---|---|---|---|
| 4,813,925 A * | 3/1989 | Anderson et al. | 604/8 |
| 4,878,492 A | 11/1989 | Sinofsky et al. | |
| 4,906,230 A * | 3/1990 | Maloney et al. | 604/95.03 |
| 5,071,424 A | 12/1991 | Reger | |
| 5,156,610 A | 10/1992 | Reger | |
| 5,166,990 A * | 11/1992 | Riccitelli et al. | 385/12 |
| 5,181,911 A | 1/1993 | Shturman | |
| 5,197,457 A * | 3/1993 | Adair | 600/104 |
| 5,256,146 A * | 10/1993 | Ensminger et al. | 604/104 |
| 5,321,501 A | 6/1994 | Swanson et al. | |
| 5,383,856 A | 1/1995 | Bersin | |
| 5,415,653 A | 5/1995 | Wardle et al. | |
| 5,447,503 A | 9/1995 | Miller | |
| 5,459,570 A | 10/1995 | Swanson et al. | |
| 5,464,395 A | 11/1995 | Faxon et al. | |
| 5,484,411 A | 1/1996 | Inderbitzen et al. | |
| 5,554,114 A | 9/1996 | Wallace et al. | |
| 5,603,720 A | 2/1997 | Kieturakis | |
| 5,709,874 A | 1/1998 | Hanson et al. | |
| 5,730,741 A | 3/1998 | Horzewski et al. | |
| 5,749,852 A | 5/1998 | Schwab et al. | |
| 5,792,415 A | 8/1998 | Hijlkema | |
| 5,827,313 A * | 10/1998 | Ream | 606/171 |
| 5,873,865 A | 2/1999 | Horzewski et al. | |
| 6,004,269 A | 12/1999 | Crowley et al. | |
| 6,134,003 A | 10/2000 | Tearney et al. | |
| 6,201,608 B1 | 3/2001 | Mandella et al. | |
| 6,241,665 B1 * | 6/2001 | Negus et al. | 600/374 |
| 6,305,378 B1 | 10/2001 | Lesh | |
| 6,322,559 B1 | 11/2001 | Daulton et al. | |
| 6,450,988 B1 | 9/2002 | Bradshaw | |
| 6,501,551 B1 | 12/2002 | Tearney et al. | |
| 6,669,655 B1 | 12/2003 | Acker et al. | |
| 6,711,444 B2 | 3/2004 | Koblish | |
| 6,745,080 B2 | 6/2004 | Koblish | |
| 2002/0055717 A1 | 5/2002 | Poncet | |
| 2002/0059827 A1 | 5/2002 | Smith | |
| 2003/0033095 A1 | 2/2003 | Svanerudh et al. | |
| 2003/0088187 A1 * | 5/2003 | Saadat et al. | 600/547 |
| 2004/0006305 A1 | 1/2004 | Hebert et al. | |
| 2004/0181128 A1 * | 9/2004 | Masters | 600/200 |

FOREIGN PATENT DOCUMENTS

| | | |
|---|---|---|
| GB | 2399017 A1 | 9/2004 |
| JP | 10500028 | 1/1998 |
| JP | 10272187 | 10/1998 |
| JP | 2000503237 | 3/2000 |

OTHER PUBLICATIONS

G.J. Tearney, et al. "Scanning single-mode fiber optic catheter-endoscope for optical coherence tomography." Apr. 1, 1996, vol. 21, No. 7, Optic Letters, pp. 543-545.
Guillermo J. Tearney, et al. "In vivo endoscopic optical biopsy tomography." Jun. 27, 1997, www.sciencemag.org, Science, vol. 276, pp. 2037-2039.
Invitation to Pay Additional Fees for PCT International Appln. No. US/2005/045509, mailed on May 12, 2006 (6 pages).
PCT Search Report and Written Opinion for PCT/US2005/045509, mailed Jul. 19, 2007, 17 pages.
Abbott Cardiovascular Systems, "Examination Report dated Dec. 27, 2011 for EP 07015146,9", (Dec. 27, 2011).
Abbott Cardiovascular Systems, Japanese office action dated Jun. 20, 2011 for JP 2007-548317.
Abbott Cardiovascular Systems, *European Examination Report dated* Feb. 28, 2013 for EP 07015145.1.

\* cited by examiner

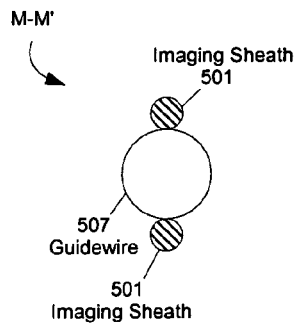 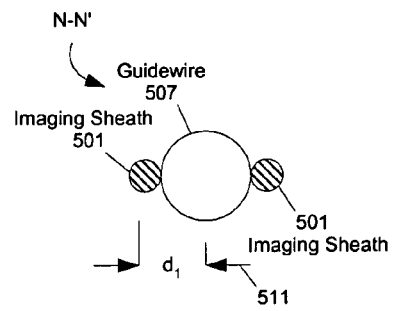 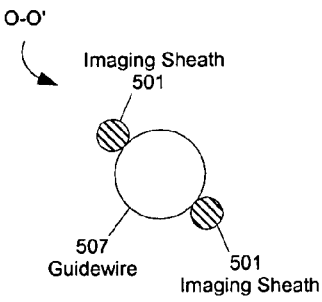
Fig. 34  Fig. 35  Fig. 36
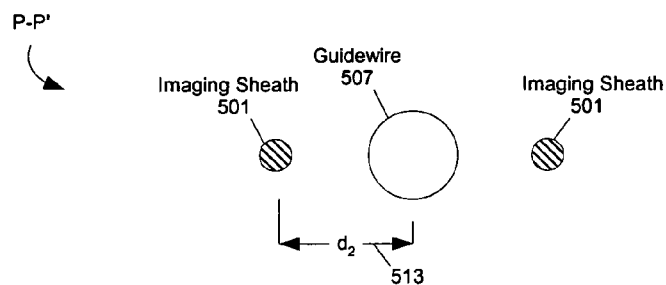
Fig. 37
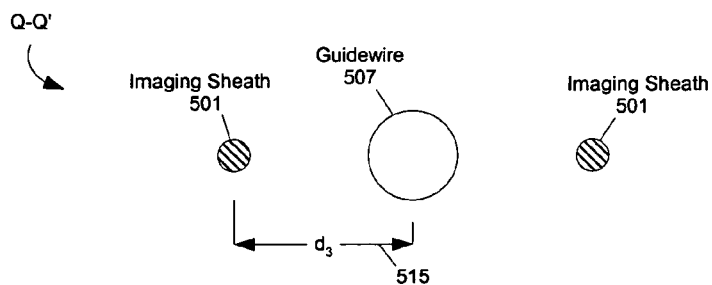
Fig. 38

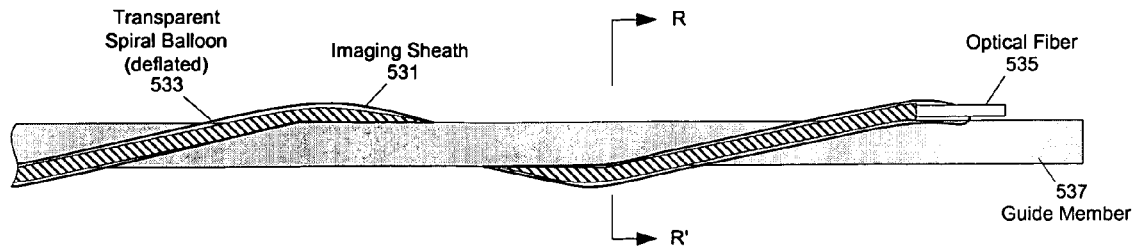
Fig. 39
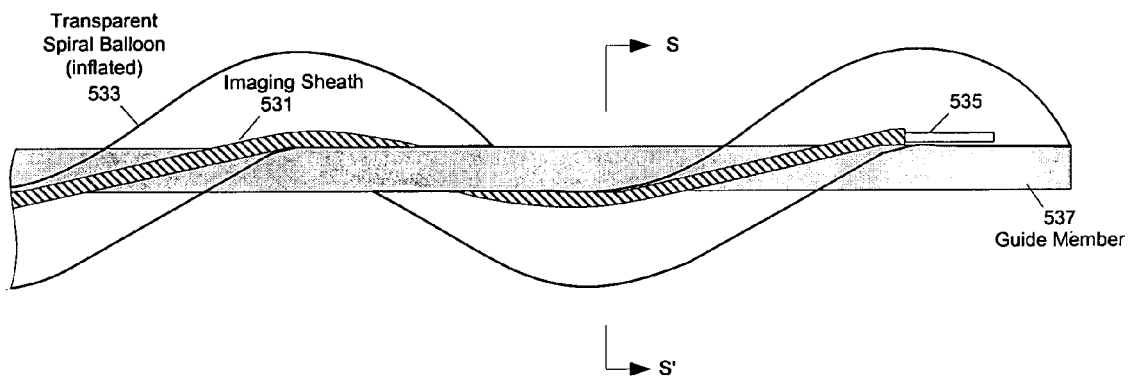
Fig. 40
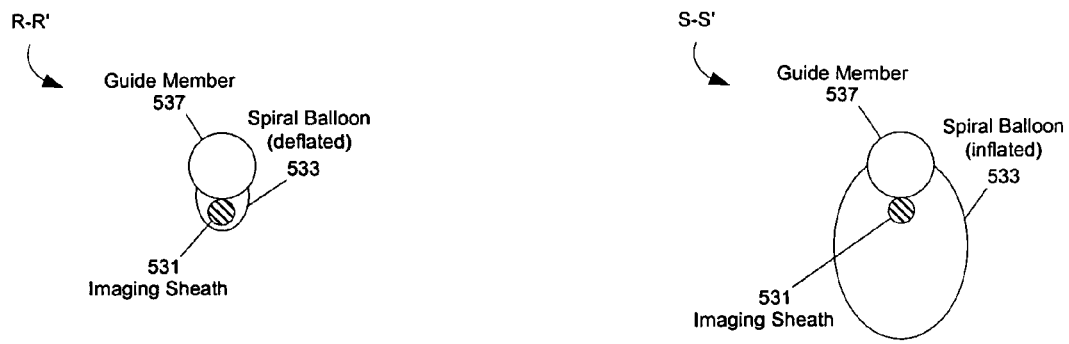
Fig. 41
Fig. 42

METHODS AND APPARATUSES FOR POSITIONING WITHIN AN INTERNAL CHANNEL

FIELD OF THE TECHNOLOGY

At least some embodiments of the present invention relate to scan imaging, treatment and/or measurement of the interior of an internal channel, such as blood vessels.

BACKGROUND

Imaging technologies have been developed for the visualization of the interior of an internal channel, such as a vein or artery. For example, current Optical Coherence Tomography (OCT) systems can image into tissue to a depth of about 1.2-1.7 mm. Analogous to ultrasound imaging, the imaging core of an OCT system projects an optical beam (e.g., a short coherence length infrared light) on the tissue and receives the reflected light from the tissue to construct an image of the tissue. An OCT based imaging system can provide higher resolution imaging than current ultrasonic systems, but to a shorter depth into the tissue.

FIG. 1 illustrates a prior art imaging assembly catheter. In FIG. 1, the imaging assembly includes a sheath (109) to house and guide the imaging core, which includes an optical fiber (107), a GRIN lens (103) (graded index lens) and a prism (101). The sheath (109) has at least a transparent window (105), through which an imaging core may project an optical beam on the tissue and receive the backscattered light. The GRIN lens (103) focuses the beam coming from an optical fiber (107); and the prism (101) directs the beam perpendicular to the longitudinal axis of the imaging sheath (109). Backscattered/reflected light from the tissues follows the reverse path to return to the optical fiber (107). Optical fibers have a core and a cladding. The light travels mostly in the core. The cladding has optical properties such that it bends any light that happens to come out of the core back into the core, so no light is lost/leaks out the side of the optical fiber. In practical systems for OCT, both the core and cladding are mostly glass with a few impurities added to get the desired optical properties. The interference amplitude between an internal system reference beam and the reflected beam from the tissue is related to the intensity of the reflected light from the tissue at the reference beam path length. By scanning the reference beam path length, the amplitude of the reflected beam is scanned at different depths into the tissue to create an image along a line into the tissue. By also rotating (113) the imaging core, a two-dimensional image slice of the tissue surrounding the prism (101) can be constructed. By withdrawing the imaging core inside the sheath (or both the sheath 109 and the imaging core), image slices of the tissue may be recorded along a length of the sheath 109 (or tissue) to provide three-dimensional tissue imaging information. This withdrawal to gather tissue images is commonly referred to as a pull back.

FIG. 2 illustrates the use of the prior art imaging assembly in scanning the interior wall of an artery. The sheath (109) is inserted into an artery (121) with the imaging core, including the grin lens (103) and prism (101). The prism directs the optical beam to a point on the artery to scan at different depths into the tissue at the point. Rotating the imaging core about the axial axis of the sheath (109) causes a scan in the circumferential direction; and moving the imaging core along the sheath (109) causes a scan in the longitudinal direction. Thus, the combined rotation and longitudinal movement of the imaging core allows the imaging core to scan the entire interior of the artery (121) for a 360-degree of circumferential image of the artery.

In a prior art system illustrated in FIG. 2, the sheath (109) is substantially straight in a straight section of the artery. Note that an artery is generally not straight; and the sheath generally follows the artery. For simplicity, the artery (or the vessel to be image) is considered straight and the sheath that follows the shape of the artery is then also considered straight. When the sheath (109) is at about the center of the artery, the distance between the sheath (109) and the artery wall is $D_A$ (123).

Current Optical Coherence Tomography (OCT) systems are not able to image more than about 1-2 mm into blood or tissue. Thus, the imaging depth of the OCT system is only about 1-2 mm. Theoretically, an OCT system may be able to image about 2-2.5 mm into tissue; but in practice, in the tissues of interest (vessel walls), a typical OCT system can image no deeper than about 1.2-1.7 mm. Thus, the blood between the artery (121) and the sheath (109) can effectively cause blockage of the light signal for the imaging of the artery wall and reduce the depth the OCT system can image into the artery wall.

Further, the wavelength of the light used in an OCT system may be short enough for the light to interact with individual red blood cells. Use of lights of longer wavelengths may avoid the red blood cell interaction but result in a loss of a desired image resolution. The red blood cells have a slightly higher index of refraction than the plasma in which they are suspended. In addition, the red blood cells are shaped like concave lenses so that the light may be redirected and refocused (diverged) by each red cell it passes through on the way to the artery wall and back from the artery wall. In addition, there are light energy losses due to absorption and path length changes due to scattering (reflection) by the red cells. Thus, the image quality decreases as the distance $D_A$ (123) between the sheath and the artery increases. It is desirable to minimize the effect of the blood's interference with the light from the imaging system as it propagates through the vessel towards the vessel wall and is reflected back to the device.

Currently, flushing is used to reduce the imaging signal (light) blockage effect of the blood. For example, saline can be injected into the artery from the catheter to temporarily remove or dilute the blood near the region to be imaged. Various techniques and devices have been used to flush blood from the imaging area with limited success. For example, flushing a coronary artery to remove blood from the field of view is normally accomplished by injecting saline into the vessel to be imaged, either through a guide catheter or a catheter/sheath that surrounds/incorporates the imaging device. However there are several problems and limitations with flushing, especially in an artery.

First, when enough saline solution or other isotonic biocompatible water-based solution is introduced to replace or dilute the blood, the amount of oxygen in the solution is very small in comparison to the amount of oxygen contained in the blood. Thus, the time window for imaging is limited by the ischemic consequences of the solution on the heart muscle (e.g., reduction in blood flow). The longer the duration of the flush, the more severe the consequences are to the heart muscle. Since imaging is generally desired in patients usually already suffering from ischemia or previous cardiac muscle ischemic tissue damage, the safe/pain-free imaging time period is short.

Second, blood flow in coronary arteries is laminar and generally tends to flow in streamlines, not mixing very rapidly with adjacent streamlines. Thus, injected solutions tend to flow in their own streamlines, leaving some areas of blood flow not completely displaced/mixed or leaving eddies of blood at branch points or at areas protected/created by the presence of the imaging device.

Third, most water-based flushing solutions have a viscosity that is significantly less than that of blood. Thus, the flow rate of the flush must exceed the normal flow rate of the blood in the vessel in order to create enough pressure in the vessel to exceed the blood pressure and displace the blood. In other words, the resistance to flow in the vessel is lower for the flush than for the blood.

As the flush replaces the flowing blood, an ever-increasing flow rate of the flush is required. For example, the decreased resistance of the flush requires more overall fluid (e.g., flush) to maintain the natural flow rate. Moreover, the vessel will dilate in response to the ischemic properties caused by an increased amount of oxygen deficient fluid in the vessel. Thus, the flush flow rate must be increased until a peak flow rate is reached, wherein the flush effectively completely replaces the blood in the artery. The volume of flush required to achieve this peak flow rate can be quite high during extended imaging periods, like those commonly used with IVUS (Intravascular Ultrasound).

Fourth, in most injection configurations, the required high flush flow rate enters the artery via a relatively small flow cross section, resulting in a very high injection velocity. This may create high velocity jets of flush, which can damage vessel walls. Additionally, the pressures and volumes required are not easily accomplished by manual injection. Therefore, an automated injection device is desirable.

Alternatively, injection of a fluid more viscous than saline (e.g., a contrast agent) may utilize a lower flow rate, but the catheter injection pressure is relatively unchanged due to the higher viscosity. A high viscosity flush also increases the time required to wash out the flush (e.g., longer ischemia time). Moreover, contrast agents are quite expensive relative to normal flushing solutions.

Several methods to deal with these problems of a typical flush have been proposed in the past. For example, oxygenated blood can be withdrawn from the patient, and certain materials may be added to the blood to increase the index of refraction of its plasma to match that of the red blood cells. This oxygenated blood, with a higher index of refraction of its plasma, can then be used as the flush. Alternatively, the materials to increase the index of refraction of the plasma may be added systemically without withdrawing any blood from the patient.

In either case, such a procedure would eliminate/effectively minimize the lens effect and the reflection effect of the red blood cells. Since the red blood cells are oxygenated, ischemia is not a problem. It has been reported that contrast can be used to make this index of refraction change to the plasma.

Changing the index of refraction on a systemic level is very difficult and can be toxic. It is easier and faster to perform the index of refraction change with blood withdrawn from the body. However, changing the index of refraction outside of the patient's body requires extra equipment and a time-consuming index matching procedure and introduces issues involving increased blood exposure (e.g., to the environment). Moreover, the streamline and injection problems discussed above would still be a challenge, and hemolysis (e.g., the destruction or dissolution of red blood cells, with subsequent release of hemoglobin) could be an added issue to consider.

Photodynamic therapy may be administered within a vessel to treat various conditions. For example, light (e.g., blue light and/or ultraviolet light) may be used to destroy (e.g., cell lysis) or treat various target tissues such as tumors and atheromas, including thin capped fibroathroma ("TCFA") or vulnerable plaque. A similar blockage of the light used in photodynamic therapies may also be a problem and may require similar saline flushing or blood dilution.

SUMMARY OF THE DESCRIPTION

Methods and apparatuses for scanning a desired portion of the interior wall of an internal channel, such as for scan imaging a blood vessel, for photodynamic therapy and for optical temperature determination, are described here. Some embodiments are summarized in this section.

In one embodiment, a catheter assembly has a distal portion that can be changed from a configuration with a small overall radius suitable for traversing the internal channel to another configuration that is suitable for scanning at least a section of the interior wall of an internal channel, such as an artery. In one example, to eliminate or reduce the blockage effect of the blood in Optical Coherence Tomography (OCT) scanning, the distal portion spirals into gentle contact with (or closer to) a section of the artery wall for imaging along a spiral path for the detection of a significant vulnerable plaque. The spiral radius may be changed through the use of a guidewire, a tendon, a spiral balloon, a tube, or others. In another example, a spiral balloon is used to clear the blood out of the way between a spiral section of the vessel wall and the imaging sheath without blocking the blood flow in the artery. In one example, a catheter assembly similar that for scan imaging is used for the effective application of light to vessel wall tissues for purposes of photodynamic therapy. To reduce the blockage effect, the core for the application of light is housed in the sheath that can spiral into gentle contact with (or closer to) a section of the blood vessel wall, or in the sheath that has a balloon inflatable to clear the blood between the sheath and the section of the blood vessel wall, to ensure that the desired section of the vessel wall was irradiated with the light to an effective/sufficient/desired degree. In one example, a similar catheter assembly is used for the effective light collecting without projecting light, such as for optical temperature determination. To reduce the blockage effect, the core for the light receiving device (e.g., such as a fiber optic assembly, a core or an imaging core for connection to optical temperature determination devices) is housed in the sheath that can spiral into gentle contact with (or closer to) a section of the blood vessel wall, or in the sheath that has an outside balloon inflatable to clear the blood between the sheath and the section of the blood vessel wall.

In one aspect of an embodiment, an elongated assembly includes: a proximal portion; and, a distal portion, the distal portion to be inserted into a vessel, the distal portion controllable through operating at the proximal portion. The distal portion includes: an elongated sheath to house a core movable within the sheath to scan a portion of the vessel; and, a guide structure coupled with the sheath. The core is capable of at least one of: projecting an optical beam onto a portion of the vessel and receiving a light from a portion of the vessel. The guide structure is controllable through the proximal portion to reduce an overall diameter of the distal portion into a first configuration; and the guide structure is controllable through the proximal portion to increase the overall diameter of the distal portion into a second configuration. In one embodiment, the sheath is in a spiral shape in the second configuration. The distal portion is to traverse the vessel in the first configuration; the core is to move along the sheath to scan for an image of the vessel in the second configuration with reduced signal blockage; and signal blockage due to blood in the vessel between outside of the spiral shape of the sheath and the vessel in the second configuration is smaller than in the first configuration without the need for flushing.

In one embodiment, the distal portion of the elongated assembly does not severely block a flow of the blood or other tissue in the vessel in the second configuration (e.g., in second configuration the distal portion does not block a flow of the blood in the vessel significantly more than in the first configuration).

In one embodiment, the assembly further includes the core housed within the sheath; the core projects an optical beam (e.g., a short coherence length light) and to receive a reflected light for optical coherence tomography.

In one example of an embodiment, a pitch length of the spiral shape is less than five times an imaging depth of the core; in one example of an embodiment, a pitch length of a spiral shape is less than a size of a significant vulnerable plaque on a blood vessel plus two times an imaging depth of the core (e.g., the depth into blood and tissue that can be imaged). In one embodiment a pitch length of the spiral is less than ten times the radius of the vessel.

In one example of an embodiment, a diameter of the spiral shape is substantially equal to a diameter of the vessel in the second configuration. Thus, the spiral gently contacts the vessel wall or is close to the vessel.

In one example of an embodiment, the distal portion of the elongated assembly has a stiffness and is formed to be a spiral shape in absence of external constrains; a straight guidewire is insertable into the distal portion of the elongated assembly to straighten the distal portion of the elongated assembly into the first configuration.

For example, the guide structure has a guidewire lumen; and the assembly further includes: a guidewire, a segment of which is operable through the proximal portion of the elongated assembly to slide within the guidewire lumen. The segment of the guidewire has a stiffness and is formed to be substantially straight in absence of external constraints. The distal portion of the elongated assembly has a stiffness and is formed to be a spiral shape in absence of external constrains. The distal portion of the elongated assembly is in the first configuration when the segment of the guidewire is in the guidewire lumen to straighten the distal portion of the elongated assembly. The distal portion of the elongated assembly is in the second configuration when the segment of the guidewire is out of the guidewire lumen. In one example, the sheath is substantially straight when in the first configuration; and a radius of the spiral shape of the sheath is substantially equal to a radius of the vessel when in the second configuration and in the vessel.

In one example of an embodiment, the distal portion of the elongated assembly has a stiffness and is formed to be substantially straight in absence of external constrains; a spiral guidewire is insertable into the distal portion of the elongated assembly to spiral the distal portion of the elongated assembly into the second configuration.

For example, the guide structure has a guidewire lumen; and the assembly further includes: a guidewire, a segment of which operable through the proximal portion of the elongated assembly to slide within the guidewire lumen. The segment of the guidewire has a stiffness and is formed to be in a spiral shape in absence of external constraints. The distal portion of the elongated assembly has a stiffness and is formed to be substantially straight in absence of external constraints. The distal portion of the elongated assembly is in the first configuration when the segment of the guidewire is out of the guidewire lumen. The distal portion of the elongated assembly is in the second configuration when the segment of the guidewire is in the guidewire lumen to spiral the distal portion of the elongated assembly. In one example, the sheath is substantially straight when in the first configuration; and a radius of the spiral shape is substantially equal to a radius of the vessel when in the second configuration and in the vessel. In one example, the assembly has a middle portion connected to the distal portion of the elongated assembly; the middle portion of the elongated assembly has a stiffness and is formed to be substantially straight in absence of external constraints; and the middle portion of the elongated assembly remains substantially straight when the segment of the guidewire is in the middle portion of the elongated assembly. In one example, another straight guidewire is inserted into the guidewire lumen to position or reposition the distal portion of the elongated assembly at different locations.

In one embodiment, the guide structure is operable at the proximal portion of the elongated assembly to: reduce a spiral length of the sheath to increase a spiral diameter of the sheath; and increase the spiral length of the sheath to reduce the spiral diameter of the sheath. In one embodiment, the guide structure is operable at the proximal portion of the elongated assembly to: reduce a number of spiral turns of the sheath to increase a spiral diameter of the sheath; and increase a number of spiral turns of the sheath to reduce the spiral diameter of the sheath.

For example, the guide structure includes: a tube; and a substantially straight guide member. A portion of the guide member is slidable into the tube. The guide member has a distal end extending outside the tube. The sheath has a distal end coupled to the distal end of the guide member. The sheath has a proximal end coupled to the tube. The sheath spirals around the guide member. The sheath wraps against the guide member in the first configuration when the portion of the guide member is out of the tube. The sheath spirals against the vessel in the second configuration when a portion of the guide member is withdrawn into the tube. In one example, the guide member is rotatable with respect to the tube; when the guide member rotates with respect to the tube in a first direction, a diameter of the spiral shape of the sheath is increased; when the guide member rotates with respect to the tube in a second direction, the diameter of the spiral shape of the sheath is decreased.

In one embodiment, the guide structure includes: a guide member; and, a tendon coupled to the guide member. The tendon bends the guide member into a spiral in the second configuration when the tendon is in tension; and the guide member has a stiffness and is formed to be substantially straight in the first configuration when the tendon is not in tension. In one example, the guide member has a tendon lumen spiraling around the guide member to house the tendon; and the sheath spirals around the guide member on an opposite side of the tendon lumen. In one example, the elongated assembly has a middle portion connected to the distal portion of the elongated assembly; the middle portion of the elongated assembly includes a plurality of tendons; the plurality of tendons in the middle portion of the elongated assembly connected to the tendon in the distal portion of the elongated assembly to provide a tension force to bend the guide member; and the tension force is distributed in the plurality of tendons in the middle portion of the elongated assembly to reduce bending moment to the middle portion of the elongated assembly due to the tension force.

In one embodiment, the guide structure includes: a guide member, which is substantially straight; and a balloon outside the guide member. The sheath spirals over the balloon; a spiral diameter of the sheath increases in the second configuration when the balloon is inflated; and the spiral diameter of the sheath decreases in the first configuration when the balloon is deflated. In one example, the balloon is of a spiral shape, spiraling around the guide member.

In one embodiment, the guide structure includes: a substantially straight guide member, the sheath spiraling around the guide member; and, a balloon containing the sheath. The distal portion of the elongated assembly is in the first configuration when the balloon is deflated; and the distal portion of the elongated assembly is in the second configuration when the balloon is inflated. In one example, the balloon spirals around the guide member.

In one aspect of an embodiment, the sheath has a spiral shape in a vessel; the sheath houses a core movable along the sheath to scan at least a spiral portion of the vessel. The core capable of at least one of: projecting an optical beam onto a portion of the vessel and receiving a light from a portion of the vessel. In one example of an embodiment, the sheath has a guidewire lumen; and a diameter of the spiral shape is substantially equal to the diameter of the vessel. In one example of an embodiment, the sheath is capable of being straighten in the vessel when a guidewire is inserted into the guidewire lumen. In one example of an embodiment, the sheath is capable of being shaped into the spiral shape in the vessel when a spiral guidewire is inserted into the guidewire lumen. In one example of an embodiment, the sheath spirals around a guide member with a distal end coupled to the guide member; the sheath has a proximal end movable along the guide member toward the distal end to increase a spiral diameter of the sheath and away from the distal end to decrease the spiral diameter of the sheath; separately or in addition, the proximal end of the sheath is rotatable around the guide member in a first direction to increase a spiral diameter of the sheath and in a second direction to decrease the spiral diameter of the sheath. In another example, the sheath spirals around a guide member with one end coupled to a distal end of the guide member and another end movable relative to a proximal end of the guide member; the proximal end of the guide member is rotatable relative to the sheath in a first direction to increase a spiral diameter of the sheath and in a second direction to decrease the spiral diameter of the sheath; separately or in addition, the guide member is movable longitudinally in one direction to reduce a spiral diameter of the sheath and in the opposite direction to increase the spiral diameter of the sheath. In one example, the proximal end is attached to the tube. In one example, the guide member has a tendon lumen spiraling around the guide member; a tendon housed inside the tendon lumen has a distal end attached to the guide member; the tendon bends the guide member into a spiral shape when the tendon is in tension; and the guide member is substantially straight when the tendon is not in tension. In one embodiment, a balloon is within the spiral shape of the sheath; the balloon is inflatable to increase a radius of the spiral shape of the sheath; and the balloon is deflatable to decrease the radius of the spiral shape of the sheath. In one embodiment, the balloon is outside a substantially straight guide member. In one example, the balloon is of a spiral shape, wrapping around the guide member. In one example, the sheath spiraling around a substantially straight guide member; a spiral balloon is mounted to enclose the sheath.

In one aspect of an embodiment, an assembly to be inserted into a vessel, includes: a sheath to house a core movable along the sheath to scan at least a portion of a vessel; and a balloon enclosing at least a portion of the sheath along the sheath. The core is capable of at least one of: projecting an optical beam onto a portion of the vessel and receiving a light from a portion of the vessel. When inflated the balloon clears at least a portion of a light path between the sheath and the vessel to reduce blockage. In one example, the balloon is of a spiral shape, spiraling around the sheath. The sheath has a stiffness and is formed to remain substantially straight when the balloon of the spiral shape is inflated. In one example, the core projects an optical beam to receive a reflected light for optical coherence tomography; and the balloon is substantially transparent to the optical beam. In one example, the balloon is movable relative to the sheath (e.g., slidable along the sheath or rotatable about the sheath).

In one aspect of an embodiment, an assembly to be inserted into a vessel includes a plurality of spiral sheaths twisted together to host one or more cores capable of at least one of: projecting an optical beam onto a portion of the vessel and receiving a light from a portion of the vessel. In one example, each of the spiral sheaths has a distal end coupled to the distal end of a guide member; and each of the spiral sheaths has a proximal end coupled to a tube. The tube is movable with respect to the guide member to change the spiral radius of the sheaths. In one example, a core is insertable from the tube into each of the plurality of spiral sheaths; in another example, each of the plurality of spiral sheaths houses an individual core.

The present invention includes apparatuses and methods, which operate these apparatuses. The methods and apparatuses can be used for scan imaging, for optical temperature determination, for photodynamic therapy, and for other applications that can benefit from reducing interference from the blood in the blood vessel. The core housed in the sheath can be used to project light, to receive light, or to project light and receive reflected light (or high frequency ultrasound).

Other features of the present invention will be apparent from the accompanying drawings and from the detailed description, which follows.

BRIEF DESCRIPTION OF THE DRAWINGS

The present invention is illustrated by way of example and not limitation in the figures of the accompanying drawings in which like references indicate similar elements.

FIGS. 31-38 illustrate an imaging assembly with a plurality of imaging sheaths according to one embodiment of the present invention.

FIGS. 39-42 illustrate an imaging assembly with a spiral balloon covering the imaging sheath according to one embodiment of the present invention.

DETAILED DESCRIPTION

Figure 1:
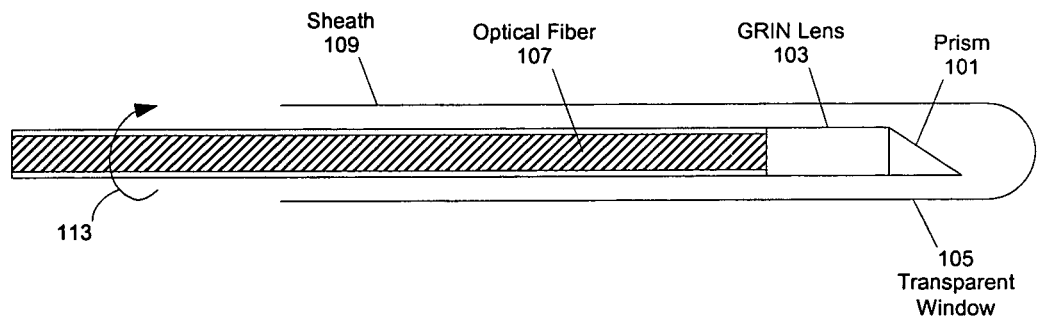
FIG. 1 illustrates a prior art imaging assembly for use with a catheter.
Figure 2:
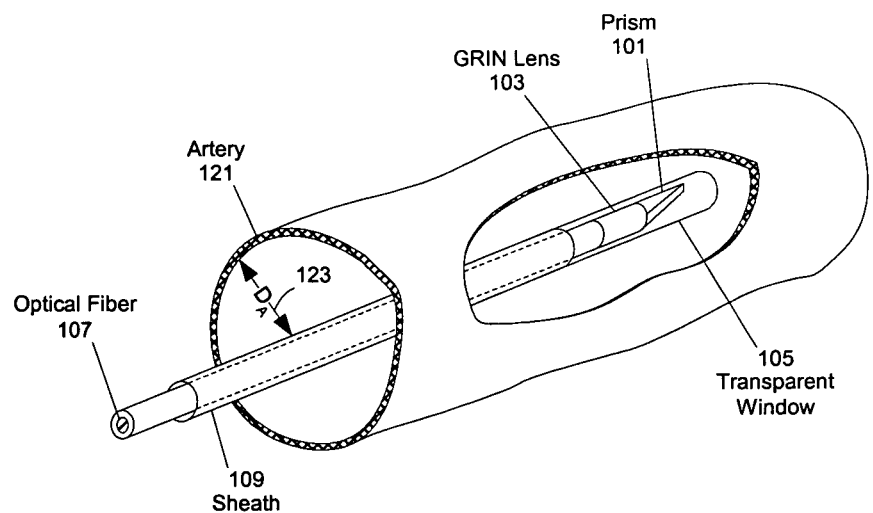
FIG. 2 illustrates the use of the prior art imaging assembly in scanning the interior wall of an artery.

The following description and drawings are illustrative of the invention and are not to be construed as limiting the invention. Numerous specific details are described to provide a thorough understanding of the present invention. However, in certain instances, well known or conventional details are not described in order to avoid obscuring the description of the present invention. References to one or an embodiment in the present disclosure are not necessarily references to the same embodiment; and, such references mean at least one.

At least one embodiment of the present invention seeks to eliminate or reduce the effect of blood on the imaging of a blood vessel without the need for flushing. While flushing the blood vessel can reduce the effect of the blood on the image quality, flushing has a few drawbacks and problems. In at least one embodiment of the present invention, an imaging sheath spirals against the blood vessel for imaging so that the imaging sheath and a desired section of the vessel wall are very close to each other, eliminating the need for flushing.

A vulnerable plaque that can rupture and cause a damaging cardiac ischemic event is highly likely large enough to occupy a significant arc section of the vessel and/or a significant length of the coronary. Thus, a full 360-degree of circumference image of the vessel is not necessary for the detection of a significant vulnerable plaque. Thus, imaging the vessel longitudinally at intervals greater than that of current OCT (Optical Coherence Tomography) or IVUS (intravascular high frequency ultrasound) systems would detect a significant vulnerable plaque.

To detect a significant vulnerable plaque it would only be necessary to image at the vessel wall in a spiral pattern down the length of the vessel with the orthogonal distance between adjacent spiral loops being shorter than the minimum length of the vulnerable plaque deemed to be significant plus 2 times the effective imaging depth. For example, if the sheath of the imaging core is positioned against the vessel wall in a spiral pattern at about a 4 mm apart in the direction orthogonal to the sheath, all of the vessel wall can be imaged when the effective imaging depth is 2 mm. If the distance is 6 mm, under the same assumptions, any vulnerable plaque about 2 mm or more in length down the vessel can be imaged and thus detected. Because the imaging sheath is in contact with (or very near) the vessel wall, flushing is not necessary.

Embodiments of the present invention provide many ways to create a percutaneous system that places the imaging sheath of an OCT system gently (to avoid wall damage or rupturing of a vulnerable plaque) against or close to the vessel wall in a manner that will not significantly reduce vessel blood flow and will thus allow imaging for periods much longer than systems that require flushing. The imaging core of an OCT system may be about 0.004-0.005 inch in diameter. An imaging sheath with a 0.001 inch wall and 0.001 inch clearance will have a diameter of 0.008 inch. Arteries that are currently accessed, imaged and treated with procedures like angioplasty are generally about 0.08" (about 2 mm) or more in Inside Diameter (ID). Thus, there is plenty of room for other components in the imaging assembly and for blood flow.

For example, one way is to form the imaging sheath with a guidewire lumen into a spiral at its distal imaging section. With the guidewire in place and the imaging core distal, the sheath is straightened by the stiffness of the guidewire and guided into a position for imaging over the guidewire. The guidewire engagement to the catheter is preferably either an RX (Rapid eXchange) or OTW (Over The Wire) style. In an RX catheter, the guidewire only engages a distal portion of the catheter, where "engage" refers to that guidewire is contained within a lumen of the catheter. In an OTW catheter, the guidewire engages the full length of the catheter. The guidewire can thus be shorter with an RX catheter. The length of the RX guidewire engagement of the catheter is chosen such that the portion of the catheter that is exposed to the vessel always engages the guidewire, so the vessel is not exposed to both the bare guidewire and the catheter at the same location. In an RX catheter, the length along the catheter where the guidewire doesn't engage the catheter (the catheter and the bare guidewire are separate and run parallel to each other) is contained within the guide catheter and exits the proximal end of the guide (and RHV). If the guidewire engagement is so short on the distal end of the catheter that both the catheter and the bare guidewire are exposed to the vessel, the engagement style is called a "tip monorail". After the withdrawn of the stiff section of the guidewire proximal to the imaging section, the sheath spirals into contact with or closer to the vessel wall. After the imaging pullback (pulling back the imaging core along the spiral sheath to scan for an image), the operator can advance the guidewire back to its former position to straighten the sheath. The imaging core can also be advanced back to its former position. Then, the sheath can be repositioned to the next imaging position in the vessel.

In a similar embodiment, the guidewire lumen may be eliminated, at least from the distal section of the catheter, if the catheter or imaging sheath is designed such that the imaging core and guidewire may replace each other within the imaging sheath. That is, with the imaging core withdrawn from the distal section, the guidewire occupies the lumen of the imaging sheath, causing the imagining sheath to straighten during catheter advancement and positioning. Once in position, the guidewire is withdrawn from the imaging sheath, allowing the imaging sheath to spiral, and then the imaging core is advanced into the imaging sheath. In this embodiment the catheter is either a single lumen device over its full length or the catheter is a single lumen device in its distal section and that lumen splits into two lumens in its proximal section.

Alternatively, the spiral is not formed into the sheath. After the straight guidewire is withdrawn, a spiral shaped guidewire (or wire or elongated material) is inserted into the guidewire lumen to cause the sheath to spiral against or closer to the vessel wall for imaging.

Another way is to form an imaging sheath section without a guidewire lumen into a spiral. The distal end of the imaging sheath is attached near the distal end of a guidewire (or a tube or a guide member that will accommodate the guidewire). The proximal end of the imaging sheath is attached to a tube, one lumen of which provides a continuous lumen to accommodate the imaging core and the other slidably (longitudinally and/or rotationally) engages the guidewire (or the tube or the guide member that will accommodate the guidewire). When the tube is held still, the guidewire can be advanced to collapse the spiral and withdrawn to expand the spiral (through changing the spiral pitch); and the guidewire can be rotated in one direction to reduce the spiral diameter and on the opposite direction to increase the spiral (through changing the number of spiral turns). Alternatively, the guidewire may be held still with respect to the body. In this case, when the tube is moved proximally (and/or rotated in the proper direction), the spiral collapses and spirals around the distal end of the guidewire (or the tube or the guide member that will accommodate the guidewire). In this position, the guidewire/catheter system can be delivered into the vessel and used to image small vessels. When the tube is moved distally (and/or rotated in the opposite direction), the spiral expands and comes in contact with or closer to the vessel wall for imaging. If the spiral does not expand enough (or expands too much) for the desired imaging due to tube distal motion, rotating the guidewire (or the tube or a guide member that will accommodate the guidewire) relative to the tube in the proper direction can adjust the size of the spiral. Thus, in general, the relative movement between the guidewire and the tube, rotationally and/or longitudinally, can be controlled to expand or collapse the spiral. In a practical system, it is typically easier to move (rotationally and/or longitudinally) the guidewire than the tube at the proximal end. Moving the tube and the proximal end of the imaging sheath can be more difficult to accomplish, as the tube has a large Outside Diameter (OD) which is subjected to pressure from outside that causes friction and difficulty in moving the tube. On the other hand, the guidewire (or guide member) is mostly inside the tube and has a small OD which limits the frictional forces required to move the guidewire (or guide member). The clearances and materials can be easily chosen so that the guide member or guidewire rotates and/or translates freely inside the tube. The proximal end of the catheter system may contain a handle with indications or marks that guide the operator in this adjustment to prevent (limit) the applied forces and displacements from damaging the catheter system and/or the vessel wall. Such a system allows a greater range of adjustment to fit the vessel and does not require a manipulation of the guidewire during the imaging procedure. The design of such a system does not require the very precise control of the flexural properties of the imaging sheath and guidewire compared to the previously described systems without a tube or guide member.

A further way is to form the imaging sheath with an imaging core lumen, a guidewire lumen and a tendon lumen(s). The catheter is constructed as an imaging deflection catheter. The tendon lumen spirals around the catheter in the distal imaging section of the catheter. The imaging core lumen spirals around the opposite side of the tendon lumen. The guidewire lumen is in the middle, between the tendon lumen and the imaging core lumen. When the catheter is in place, pulling on the tendon of the deflection catheter causes the imaging section to form into a spiral and come into contact with or move closer to the vessel wall for imaging. The guidewire may be withdrawn from the imaging section prior to pulling on the tendon, if desired. As before, the guidewire lumen can be eliminated, at least from the distal section of the catheter, when the catheter or imaging sheath is designed such that the imaging core and guidewire can replace each other within the imaging sheath.

A further way is to place a spiral balloon on a catheter and put an imaging sheath on the outside of the balloon. The spiral balloon allows blood flow and positions the imaging sheath (and the imaging core) on or near the vessel wall when inflated. Alternatively, the imaging sheath may spiral on the outside of a regular balloon on a reperfusion catheter chassis. Although the regular balloon causes more blockage of the blood flow in the vessel, the reperfusion lumen of the catheter chassis provides a channel for blood flow in the vessel. In systems with the imaging sheath positioned on the outside of balloon, it is preferred that the imaging sheath be attached at or near the distal end of the balloon's major Outside Diameter (OD) and the imaging sheath be designed to accommodate the length changes caused by the balloon's inflation. This can be done in various manners, but the simplest is to form the imaging sheath into one or more telescoping sections and to either loosely constrain the imaging sheath to the balloon with loops or a channel(s) or to attach the imaging sheath to the balloon OD between telescoping sections.

Alternatively, the imaging sheath is within a transparent/translucent spiral balloon. The shape and length of the imaging sheath does not change as the balloon is inflated or deflated. When the balloon is inflated, the spiral balloon pushes the blood out put the way between the imaging sheath and a spiral section of the vessel wall but still allows blood flow in the vessel. The balloon may be deflated, repositioned (rotated and/or moved longitudinally relative to the vessel) and re-inflated for imaging different spiral sections of the vessel wall.

The imaging sheath (a lumen wall, an imaging assembly wall, a guide member or a portion of the imaging core) can contain a radiopaque marker(s), radiopaque filler material and/or OCT detectable features that can be used to identify where in the spiral a vulnerable plaque is imaged. Thus, in conjunction with fluoroscopy, an imaged feature of the vessel wall may be located relative the vessel anatomy for treatment and/or further examination. Fluoroscopy may also aid in re-positioning the imaging assembly/catheter to obtain a better image of a vessel feature. If the treatment is to be a photodynamic treatment where the light is sent to the treatment site via the imaging core, OCT detectable features of the vessel and/or the imaging sheath can provide sufficient location information to guide the treatment.

Further details for various embodiments of the present invention are described below. From this description, a person skilled in the art can envision many variations in the scanning procedures, the designs of the sheath, designs of the imaging assembly and the designs of the formed or manipulated spiral based on the examples provide below.

Figure 3:
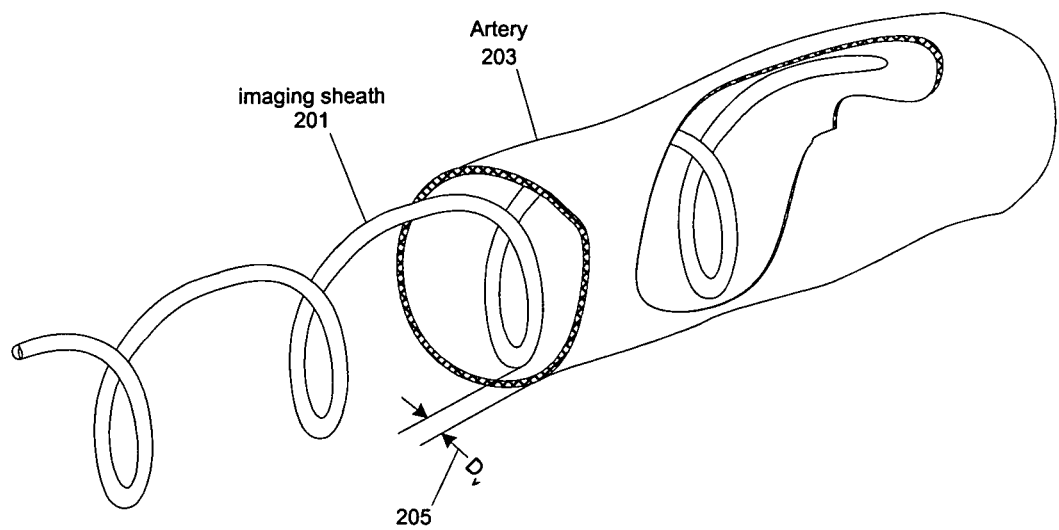
FIG. 3 illustrates an imaging sheath according to one embodiment of the present invention.

FIG. 3 illustrates an imaging sheath according to one embodiment of the present invention. In FIG. 3, the imaging sheath (201) spirals within the artery (203) so that the imaging sheath (201) spirals very close to or in contact with the artery wall. Since the spiral radius of the imaging sheath (201) is substantially equal to the radius of the artery (203), the distance $D_v$ (205) between the outside of the spiral of the imaging sheath and the artery wall is significantly reduced. Thus, at least a spiral path around the artery wall can be scanned from the imaging sheath at close range without a significant blockage effect from the blood. In FIG. 3, for illustration purpose, the artery is shown as straight. It is understood that an artery or vessel is generally not straight. However, it is understood that in this description, the portion of the vessel to be imaged is substantially straight when compared to the spiral of the imaging sheath.

In one embodiment of the present invention, the spiral of the imaging sheath gently touches the artery or vessel wall so that the distance $D_v$ is zero or almost zero along a portion of the length of the imaging sheath. Indeed, the spiral of the imaging sheath may gently deform the wall of the vessel, such that the vessel wall may conform to cover a portion of the OD of the imaging sheath.

In one embodiment of the present invention, the shape of the imaging sheath is controllable to have one configuration as illustrated as in FIG. 3 for the imaging of the artery and another configuration which has a substantially smaller overall radius so that the imaging sheath can be more easily and atraumatically moved within the artery/vessel or more easily delivered to the artery/vessel by conventional devices such as guide catheters and guidewires.

Examples of using an imaging core that projects and receives a beam of a short coherence length infrared light for OCT scanning (e.g., through a GRIN lens and a prism) are illustrated and/or discussed in many embodiments. Any light-based image scanning or photodynamic therapy system can also be used with these embodiments. It is understood that any light-based imaging scanning system known in the art can be used. Further, it is understood that other forms of light delivering devices, such as photodynamic therapy light delivery devices, or other forms of light collecting devices, such as optical temperature determination devices, can be used with the embodiments of the present invention. Furthermore, other types of imaging scanning systems (e.g., high frequency ultrasound based systems) may also be used with the present invention. Thus, the term "imaging core" includes light delivering devices (e.g., as in photodynamic therapy), light receiving devices (e.g., as for optical temperature determination), light (electromagnetic waves, visible or not) delivering and receiving devices (e.g., as in an OCT system), and delivering and/or receiving devices for energy that propagates in waves (e.g., high frequency ultrasound) and thus suffer from problems due to interactions with blood.

Additionally, many of the embodiments of the present invention can also be used with other devices where proximity to the vessel wall is desired. For instance, a temperature sensor (i.e. a thermocouple, a thermistor) may be used to measure vessel wall temperature changes to help identify a vulnerable plaque. In another instance the imaging sheath may be made of a material that is permeable to a chemical that it is desired to detect in the vessel wall and the core contains at least a portion of a detector system for that chemical.

Figure 4:
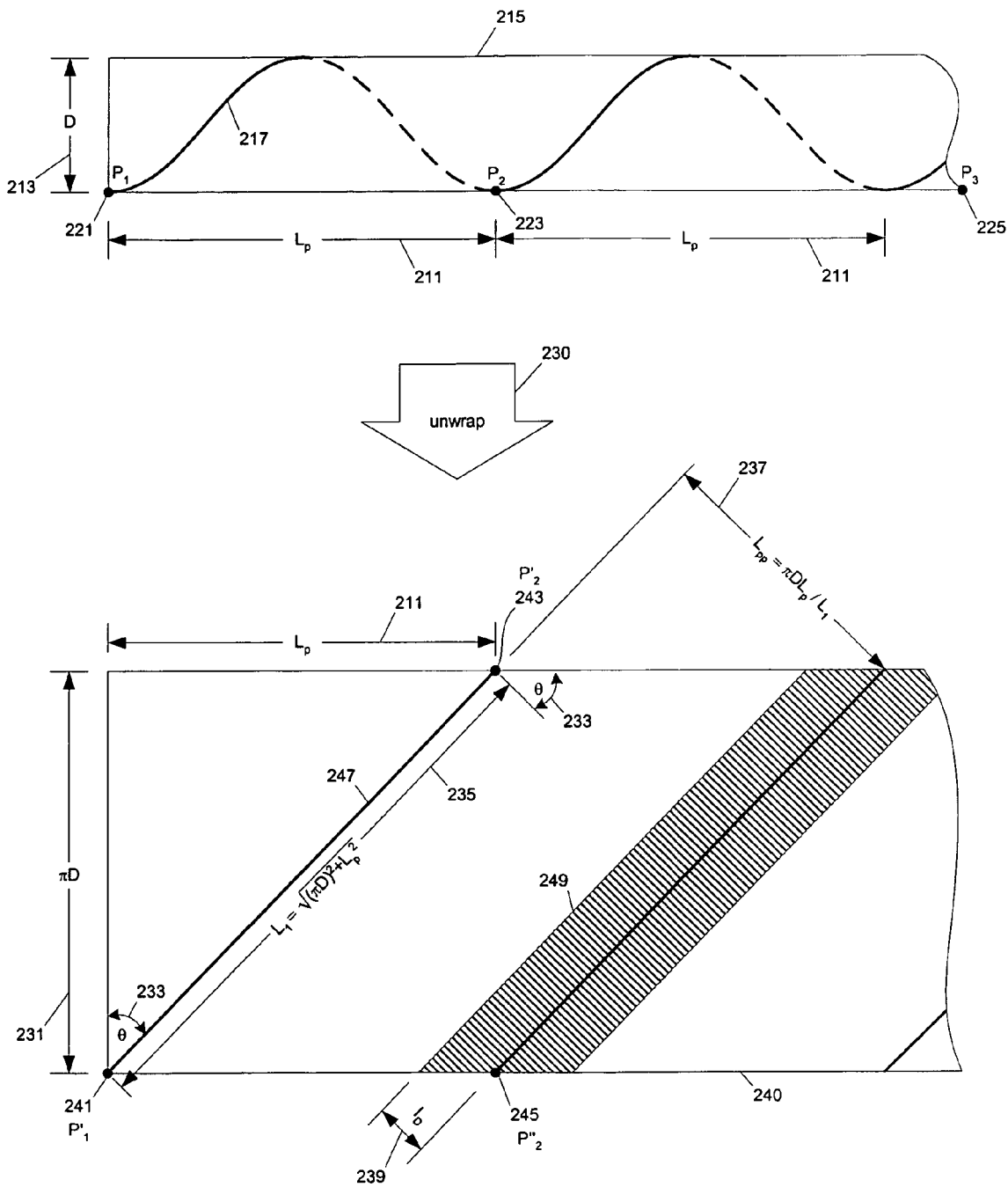
FIGS. 4-5 show geometric relations of a spiral, which may be used in designing an imaging sheath according to one embodiment of the present invention.
Figure 5:
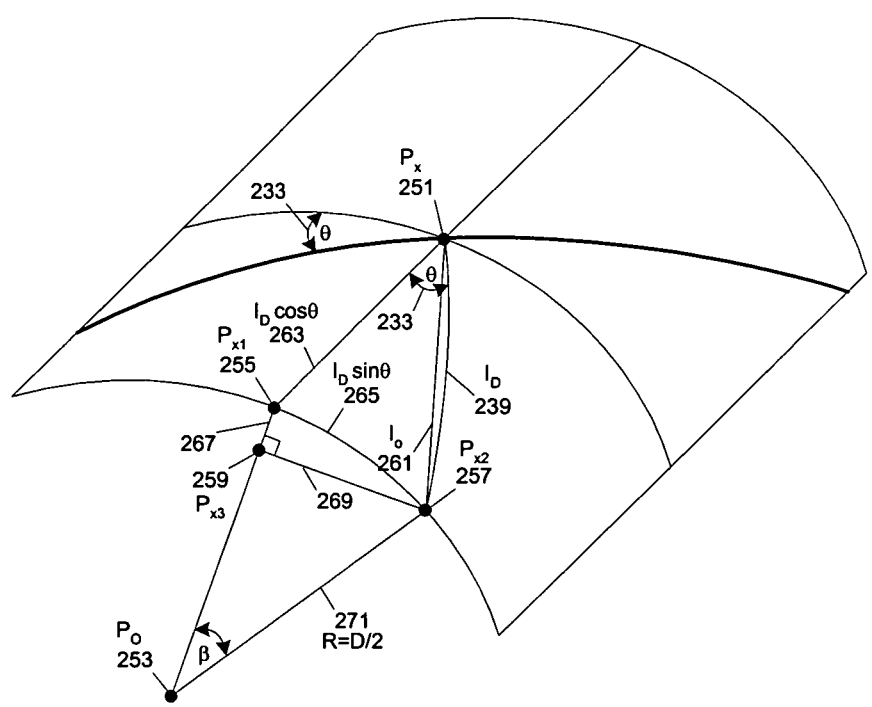

FIGS. 4-5 show geometric relations of a spiral, which may be used in designing an imaging sheath according to one embodiment of the present invention. The spiral (217) wraps around a cylindrical surface (215). The cylindrical surface (215) has a diameter D (213), which is equal to the spiral diameter of the spiral (217). The spiral length of one turn of the spiral (e.g., from point $P_1$ (221) to point $P_2$ (223)) is the pitch length $L_p$ (211) of the spiral (217).

A cylindrical surface (e.g., 215) can be unwrapped as a flattened surface without stretching. If the cylindrical surface (215) is cut along the straight line $P_1P_3$ (221 to 225) and unwrapped (230) as a flattened surface 240. The portion of the spiral 217 between points $P_1$ (221) and $P_2$ (223) becomes a straight line (247) between points $P'_1$ (241) and $P'_2$ (243) on the flattened surface 240.

Thus, the wind angle θ can be determined from the pitch length $L_p$ of the spiral and the circumference πD. The length of the straightened imaging sheath for each turn of the spiral is $L_1 = [(\pi D)^2 + L_p^2]^{1/2}$.

In FIG. 4, one can see the following geometric relations.

$$\sin \theta = L_p/L_1$$

$$\cos \theta = \pi D/L_1$$

$$\tan \theta = L_p/\pi D$$

Since $(\pi D)^2 = L_1^2 - L_p^2$, one can see that for a given length of imaging sheath (e.g., $L_1$), the spiral radius (D/2) increases when the spiral length ($L_p$) is reduced; similarly, the spiral diameter (D) decreases when the spiral length ($L_p$) is increased.

The relation between the total length ($L_T$) of the straightened imaging sheath and the length of the straightened imaging sheath for each turn of spiral is:

$$L_1 = L_T/N_T$$

where $N_T$ is the total number of spiral turns.

Thus, reducing the number of spiral turns increases the length of the imaging sheath for each spiral turn, which increases the spiral diameter if the pitch length $L_p$ is kept constant. Similarly, increasing the number of spiral turns decreases the length of the imaging sheath for each spiral turn, which decreases the spiral diameter if the pitch length $L_p$ is kept constant.

The distance between the adjacent turns of the spiral on the flattened surface 240 is $$L_{pp} = L_p \cos \theta = \pi D L_p/L_1$$

Since the imaging system scans perpendicular to the longitudinal direction, a strip (249) on the flattened surface (240) is scanned and imaged. If the half width of the strip (249) is $I_D$ (239), the gap width that is not scanned is $$W_n = L_{pp} - 2 I_D = \pi D L_p/L_1 - 2 I_D$$

Let the diameter of a significant vulnerable plaque be $S_p$. Thus, the scanning along the spiral will not miss the vulnerable plaque, if $$W_n < S_p.$$

The half width $I_D$ (239) of the imaged strip (249) is measured on the flattened surface (240). FIG. 5 shows the geometric relation between the half width $I_D$ (239) of the imaged strip and the imaging depth $I_o$ (261). The projection of $I_D$ (239) along the longitudinal direction is $I_D \cos \theta$ (263); and the projection of $I_D$ (239) along the circumference is $I_D \sin \theta$ (263). Since the angle β (253) is $$\beta = (I_D \sin \theta)/R$$

where R=D/2 is the radius of the spiral, the lengths of line segments $P_{x3}P_{x1}$ (267) and $P_{x3}P_{x2}$ (269) are (R−R cos β) and (R sin β) respectively. Thus, the relation between the imaging depth $I_o$ and the half width $I_D$ is:

$$I_o^2 = (I_D \cos \theta)^2 + (R - R \cos \beta)^2 + (R \sin \beta)^2$$

Thus, when the imaging depth $I_o$ is known, the above equation can be used to determine the half width of the imaged strip. When the angle β is small, $I_D$ is approximately equal to $I_o$.

When the spiral surface is not on the surface of the blood vessel, which has a radius of $R_v$, the relation between the imaging depth $I_o$ and the half width of the imaged strip is:

$$I_o^2 = (I_D \cos \theta)^2 + (R - R_v \cos \beta)^2 + (R \sin \beta)^2$$

where $$\beta = (I_D \sin \theta)/R_v$$

Although the above spiral geometry illustrates a perfect spiral, it is understood that in this description the term "spiral" is also for shapes that approximate a perfect spiral, which may have a pitch length varying from point to point and a spiral radius varying from point to point. Thus, the spiral radius and spiral pitch length for a general spiral discussed in this description are average measurements of a local region of the spiral. This geometric description provides the basis for determining the desired or resulting imaging conditions of spiral imaging sheath designs in vessels.

In one embodiment of the present invention, the spiral of the imaging sheath is to gently contact the interior of the blood vessel so that R is approximately equal to $R_v$. In one embodiment, the pitch length of the spiral is smaller than the size of a significant vulnerable plaque in a blood vessel wall plus two times an imaging depth of the imaging core such that at least a portion of the significant vulnerable plaque will be in the imaged strip. Alternatively, the pitch length may be longer, such that a significant vulnerable plaque may not be imaged. To ensure that a significant vulnerable plaque is detected the spiral of the imaging sheath is moved into different positions (e.g., rotated with respect to the blood vessel or sliding/translated along the length of the blood vessel for a distance not equal to the pitch length, such as half the pitch length or one third of the pitch length) to image different spiral paths (imaged strip) along the blood vessel wall for a more complete scan. As previously discussed, it is preferred that the radius of the spiral be reduced prior to moving to a different position in the vessel and then returned to the larger radius for imaging. Alternatively, multiple spiral imaging sheaths/imaging cores can be used.

Figure 6:
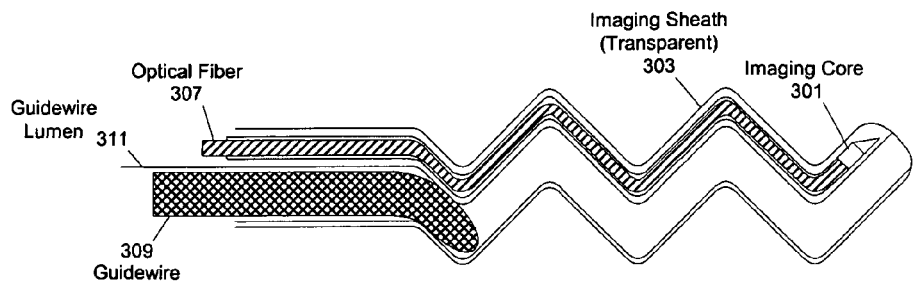
FIGS. 6-8 illustrate an imaging assembly with a preformed spiral imaging sheath according to one embodiment of the present invention
Figure 7:
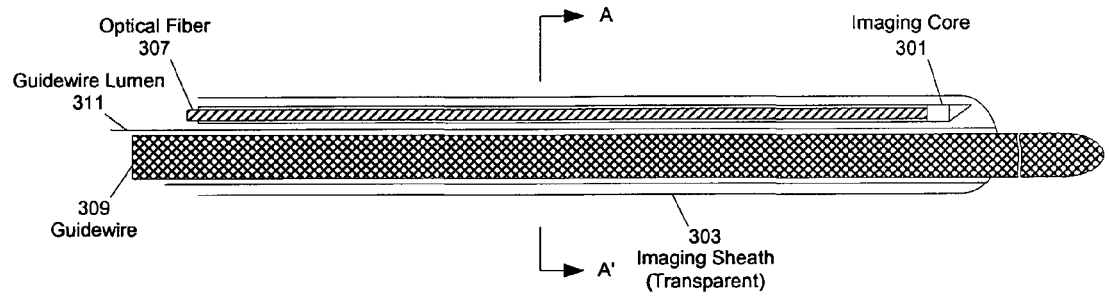
Figure 8:
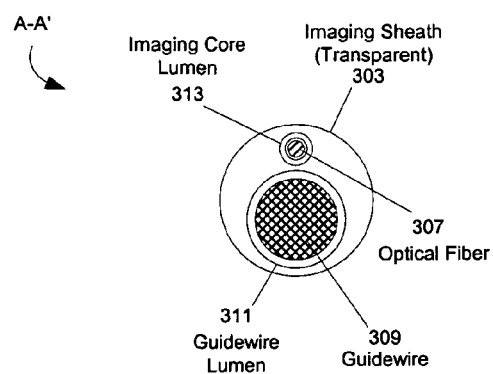

FIGS. 6-8 illustrate an imaging assembly with a preformed spiral imaging sheath according to one embodiment of the present invention. FIG. 6 shows the spiral shape of the distal end of the imaging sheath (303) in the absence of external constraints, such as the presence of the guidewire or the ID of the vessel. The distal portion of the imaging sheath (with a guidewire lumen) is formed into a spiral. The imaging sheath is substantially transparent/translucent (or has a substantially transparent/translucent window on the outside of the spiral) to allow the imaging core 301 to scan and image the wall of the blood vessel. The proximal end of the optical fiber 307 can drive the imaging core (301) to rotate and move along the imaging sheath for a spiral scan.

In one embodiment, the spiral forming process, and/or the dimensions and/or material stiffnesses of the imaging sheath (303) are manipulated to ensure that imaging core lumen (313) has a natural tendency to be on the outside of the spiral/nearest the vessel wall. For instance, the spiral can be formed by heat setting a thermoplastic sheath (303) into a spiral using a spiral (or straight) mandrel in the imaging core lumen (313) and another mandrel with a smaller spiral radius in the guidewire lumen (313). With sufficient stiffness and/or a great enough difference in spiral radius, the mandrels will force the guidewire lumen (311) to the inside of the spiral and the imaging core lumen (303) to the outside of the spiral (e.g., in a configuration similar to that illustrated in FIG. 12 but in absence of the guidewire 349).

In one embodiment, the guidewire lumen goes distal to the distal end of the sheath; and the guidewire lumen is open at the distal end of the sheath. A guidewire is used to deliver the imaging assembly to the desired location in the vessel. After the guidewire is positioned across the vessel region of interest, the imaging assembly (RX or OTW) is tracked over the guidewire to the vessel region of interest. The guidewires that have relatively short floppy distal ends (e.g., Ironman series of guidewires from Guidant Corporation) can work better than "normal" guidewires (e.g., Hi-Torque Floppy series of guidewires from Guidant Corporation).

Figure 14:
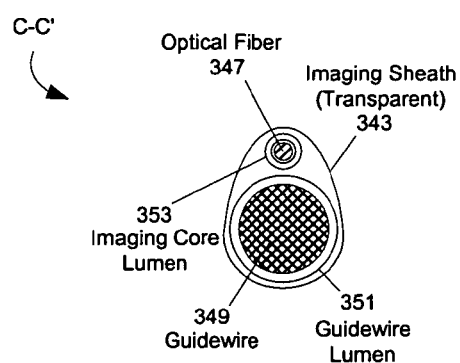

In one embodiment, an OCT imaging core/optical fiber is about 0.004-0.005" in OD and a guidewire for this application is about 0.014" in OD. Thus, the OD of the guidewire is roughly 3 times the OD of the optical fiber/imaging core. Further, the OD of the imaging sheath in the cross-section view does not have to be circular. The OD of the imaging sheath in the cross-section view can be circular or noncircular, such as oval or egg shaped (e.g., as illustrated in FIG. 14).

FIG. 7 shows the imaging sheath (303) of FIG. 6 being temporarily straightened by a guidewire (309). The guidewire (309) is of a substantially straight shape, having a stiffness great enough in a section near its distal end so that when that section of the guidewire (309) is inserted into the spiral portion of the imaging sheath (303), the spiral portion of the imaging sheath (303) is substantially straightened. When the spiral portion of the imaging sheath (303) is straightened, the overall diameter of the spiral of the imaging sheath (303) is reduced to allow the positioning of the imaging sheath (303). For example, the imaging sheath (303) can be inserted into the blood vessel via a guide catheter and over the guidewire (309) and positioned across a target location; or, the imaging sheath (303) may be repositioned after a scan. Once the imaging sheath (303) is at a desired position, the guidewire (309) can be withdrawn until only its distal floppy end is in the spiral formed distal section of the imaging sheath (303) or pulled out of the spiral formed section of the imaging sheath (303) to allow the distal end of the imaging sheath (303) to come back to the spiral shape.

In one embodiment, when the straight guidewire is in the imaging sheath, as illustrated in FIG. 7, the overall structure of the distal portion is still flexible enough to follow the guidewire and pass though turning points of a blood vessel (e.g., a vein or artery). Thus, the stiffness of the guidewire and the stiffness of the imaging sheath are calibrated so that at least a section of the guidewire can straighten the spiral of the imaging sheath if that distal portion is in a straight section of the vessel and that distal portion can still bend when it encounters the vessel wall or bend with the guidewire to pass the turning points of the blood vessel to reach a target location without causing damage to the blood vessel wall. In one embodiment, the imaging sheath 303 may include a distal tapered tip/soft tip to aid it in following the guidewire into position in the curved vessel anatomy in the manner currently employed to aid in the atraumatic positioning of angioplasty catheters.

In one embodiment of the present invention, the preformed spiral radius of the imaging sheath is larger than or approximately equal to the radius of the blood vessel at the target location so that, when the guidewire is withdrawn, the imaging sheath gently spirals against or very close to the vessel wall.

FIG. 8 illustrates a cross section view along A-A' in FIG. 7. The imaging sheath is transparent at least for the back portion of the spiral to allow the passage of the light for OCT scanning. An imaging core lumen (317) allows the optical fiber (307) to move longitudinally and rotate within the imaging sheath (303). A guidewire lumen (311) allows the guidewire (309) to be inserted to straighten the spiral portion of the imaging sheath or withdrawn to allow the imaging sheath to form a spiral.

Alternatively, the imaging core and the guidewire may share the same distal lumen. To reposition the distal portion of the imaging sheath at a target location, imaging core is withdrawn from the lumen and the guidewire is advanced into the lumen. To scan the vessel wall, the guidewire is withdrawn out of the lumen; and the imaging core is advanced into the lumen (e.g., for an imaging pullback).

Figure 9:
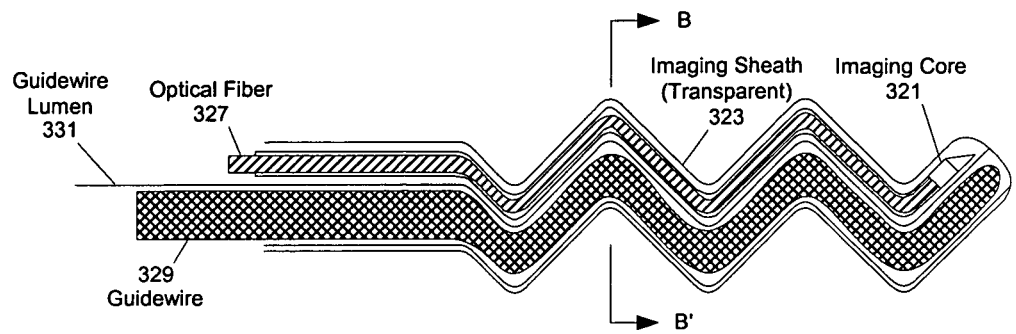
FIGS. 9-14 illustrate imaging assemblies with a preformed spiral guidewire according to embodiments of the present invention.

FIGS. 9-14 illustrate imaging assemblies with a preformed spiral guidewire according to embodiments of the present invention. FIG. 9 shows a spiral guidewire (329) forcing the distal portion of an imaging sheath (323) into a spiral shape. The guidewire (329) is of a spiral shape in the distal portion, having a stiffness greater than the stiffness of the distal portion of the imaging sheath so that when the guidewire is inserted the distal portion of the imaging sheath (303) is temporarily forced into a spiral shape. When the imaging sheath is positioned at the target location and forced into the spiral shape, an imaging core (321) can be controlled though an optical fiber (327) to perform a spiral scanning. The imaging sheath is substantially transparent/translucent (or has a substantially transparent/translucent window on the back of the spiral) to allow the imaging core 301 to scan and image the wall of the blood vessel.

Figure 10:
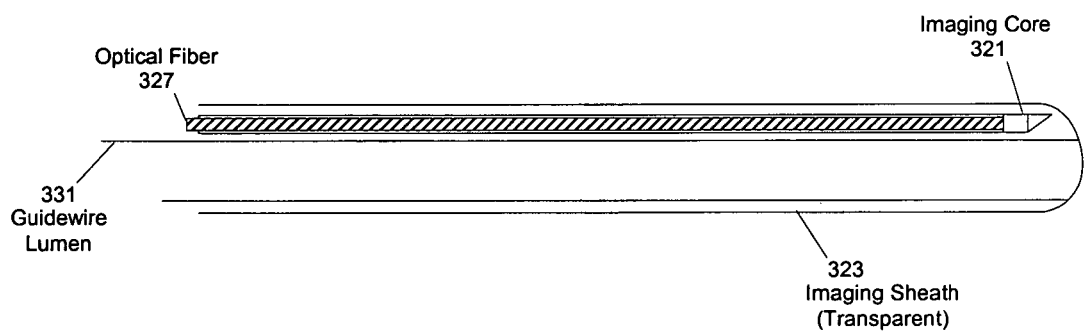

FIG. 10 shows the imaging sheath of FIG. 9 being in a substantially straight shape after the spiral guidewire is removed. When the distal portion of the imaging sheath (303) is straightened, the overall diameter of the imaging sheath is reduced to allow the placement and repositioning of the imaging sheath. For example, the imaging sheath can be inserted into the blood vessel and positioned to a target location; or, the imaging sheath may be repositioned after a scan. The distal end of the imaging sheath (323) may include a fixed guidewire tip and/or a bent end to aid in the subselection of the desired vessel branch. Alternatively, a conventional (straight) guidewire with various distal end configurations can be used in the guidewire lumen to guide the imaging sheath (323) to the target location in the conventional manner. Once the imaging sheath is at a desired location, the spiral guidewire can be inserted into the imaging sheath to force the imaging sheath to a spiral shape.

In one embodiment of the present invention, the preformed spiral radius of the guidewire is larger than or approximately equal to the radius of the blood vessel at the target location so that, when the guidewire is inserted, the imaging sheath gently spirals against (or close to) the vessel wall.

In one embodiment of the present invention, the stiffness of the spiral guidewire is smaller than a proximal portion of the imaging sheath such that when the spiral guidewire is in the proximal portion of the imaging sheath, the spiral guidewire is temporarily straightened/has less of a spiral. Thus, the spiral guidewire will only substantially bend the distal portion of the imaging sheath into a spiral of the desired radius, but not the proximal portion of the imaging sheath. Alternatively, the proximal portion of the imaging sheath is covered by a tube or a guide catheter, which temporarily straightens the spiral portion of the guidewire when the spiral portion of the guidewire is not inserted into the distal portion of the imaging sheath. The overall stiffness of the catheter assembly is calibrated so that the assembly is flexible enough to be delivered in a blood vessel without causing damage to the vessel wall.

Figure 11:
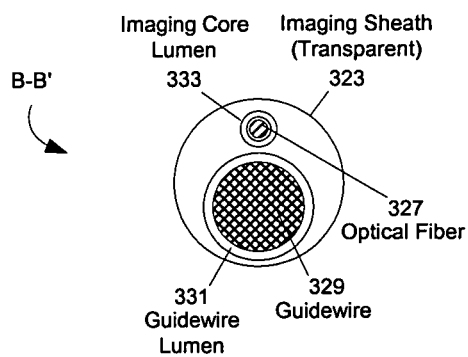

FIG. 11 illustrates a cross section view along B-B' in FIG. 9. The imaging sheath (323) is substantially transparent/translucent for at least a portion of the spiral to allow the passage of the light for OCT scanning. An imaging core lumen (333) allows the optical fiber (327) to move longitudinally and rotate within the imaging sheath. A guidewire lumen (331) allows the guidewire (329) to be inserted to force the distal portion of the imaging sheath into a spiral or withdrawn to straighten the imaging sheath. Guidewire lumen (331) may also allow the imaging sheath (323) to follow a more conventional guidewire during the initial positioning of the imaging sheath (323) in the vessel.

Figure 12:
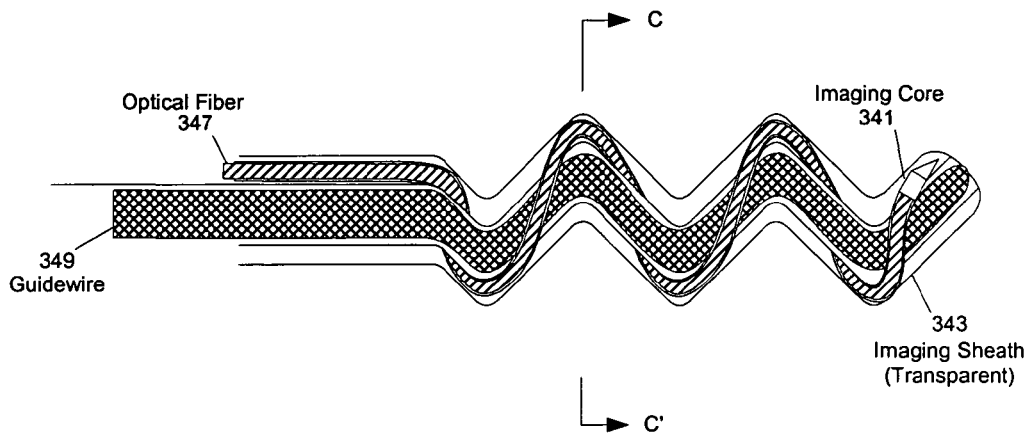
Figure 13:
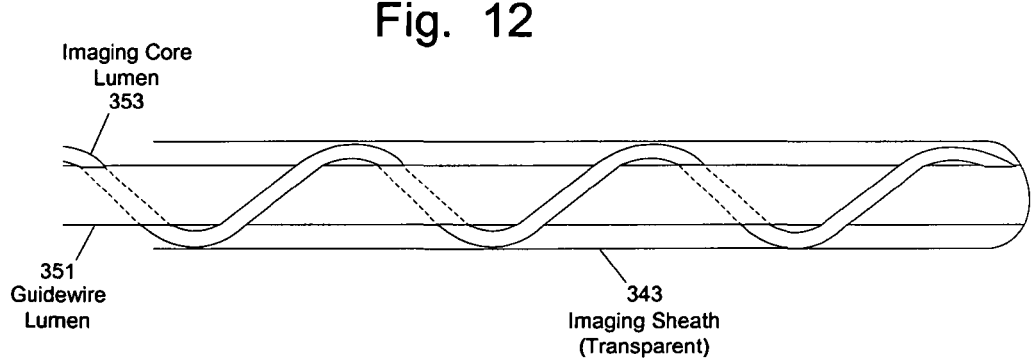

FIGS. 12-14 illustrate an embodiment in which the imaging core lumen spirals around the guidewire lumen. FIG. 12 shows a spiral guidewire (349) forcing the distal portion of an imaging sheath (343) into a spiral shape. The guidewire (349) is of a spiral shape in the distal portion, having a stiffness greater than the stiffness of the distal portion of the imaging sheath so that when the guidewire is inserted the distal portion of the imaging sheath (343) is temporarily forced into a spiral shape.

FIG. 13 shows that the imaging core lumen (353) spirals around the guidewire lumen (351) when the spiral guidewire is not inserted into the distal portion of the imaging sheath and the imaging sheath is substantially straight. The imaging core lumen (353) spirals around the guidewire lumen (351) when the imaging sheath is substantially straight. Thus, when the spiral guidewire (349) is inserted into the guidewire lumen (351) in the distal portion, the imaging core lumen spirals outside the guidewire lumen, as illustrated in FIG. 12; and the spiral guidewire is inside the imaging core lumen so that the guidewire is not in the way between the imaging lumen and the vessel wall.

FIG. 14 illustrates a cross section view along C-C' in FIG. 12. The imaging sheath (343) is substantially transparent/translucent for at least a portion of the spiral to allow the passage of the light for OCT scanning. An imaging core lumen (353) allows the optical fiber (347) to move longitudinally and rotate within the imaging sheath (343). A guidewire lumen (351) allows the guidewire (349) to be inserted to force the distal portion of the imaging sheath into a spiral or withdrawn to straighten the imaging sheath. Guidewire lumen (351) may also allow the imaging sheath (343) to follow a more conventional guidewire during the initial positioning of the imaging sheath (343) in the vessel.

Figure 15:
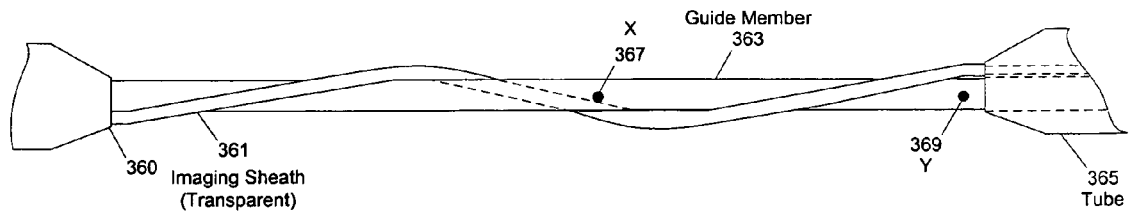
FIGS. 15-17 illustrate an imaging assembly with a tube according to one embodiment of the present invention.
Figure 16:
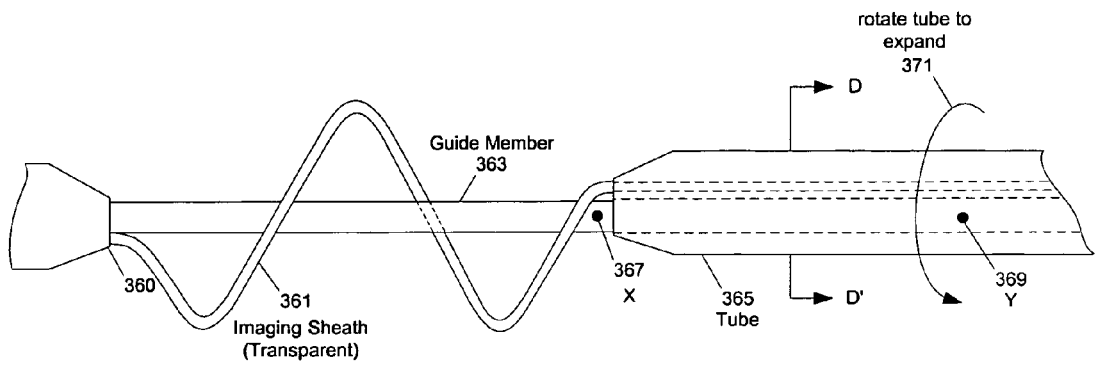
Figure 17:
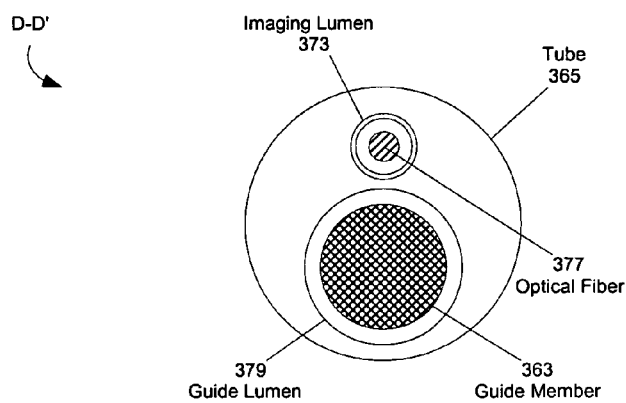

FIGS. 15-17 illustrate an imaging assembly with a tube according to one embodiment of the present invention. FIG. 15 illustrates a configuration in which an imaging sheath (361) is tightly wrapped in a spiral around a guide member (363). The distal end (360) of the imaging sheath (361) is fixed to the guide member (363); and the other end of the imaging sheath (361) is fixed to the tube (365). The guide member (363) is slidable into the tube to reduce the distance between the two ends of the spiral imaging sheath (361). In FIG. 15, one end of the tube (365) is close to the point Y (369) of the guide member. The spiral of the imaging sheath (363) is elongated so that the spiral radius of the imaging sheath (363) is small. Thus, the overall radius of the distal portion of the imaging assembly is small so that the distal portion of the imaging assembly can be moved easily within an internal channel to a target position.

The distal end of the tube (365) is tapered so that there is no sharp edge to contact the vessel. The distal end (360) of the imaging sheath (361) is tapered to a larger OD, made of materials that have a higher modulus distally and/or contain a tapered stiffening device (a wire(s), braid, etc.) so the spiral will gradually curve away from the guide member and not bend at a sharp angle when the spiral is expanded. The proximal end of the imaging sheath connects to the distal end of the tube (365) in a similar fashion to avoid being bent at a sharp angle. The distal end of the guide member can be made more conventional/atraumatic by extending it further distal of its connection with the imaging sheath. When the guide member is a guidewire, the distal end of the guide member can be the short (short is preferred) floppy tip of the guidewire. When the guide member is a tube that accommodates a guidewire in its ID, the distal end of the guide member can be a soft tapered tip like those incorporated on angioplasty catheters. When the guide member is a shaft (no ID), the distal end of the guide member can be a soft tapered tip with a bent end and/or a fixed guidewire.

The guide member (363) can be just a guidewire that can be pulled into or pushed out of the tube (365). Alternatively, the guide member can be a tube or a catheter that accommodates the guidewire and that can be pulled into or pushed out of the tube (365) through pulling or pushing the guidewire.

In FIG. 16, when the tube (365) is moved towards the distal end of the guide member, the guide member (363) slides into the tube (365). The point Y (369) of the guide member is inside the tube (365); and the distal end of the tube (365) is close to the point X (367) of the guide member. Since the spiral of the imaging sheath (361) has one end attached to the distal end (360) of the guide member (363) and another to the tube (365), the spiral length of the imaging sheath (361) is reduced. Thus, the spiral radius of the imaging sheath (361) is increased. The relative position of the guide member with respect to the tube can be adjusted to control the spiral length and spiral radius of the imaging sheath (361). The spiral radius can be adjusted so that the spiral of the imaging sheath gently contacts the vessel wall. Then, a spiral section of the vessel wall can be imaged with reduced signal blockage from blood in the vessel since the imaging sheath is brought close to the spiral section of the vessel wall.

Further, the tube can be rotated (371) with respect to the guide member to change the number of spiral turns of the imaging sheath (363). When the tube (365) is rotated with respect to the guide member (363) in the direction as shown in FIG. 16 (and/or the guide member is rotated with respect to the tube in the opposite direction), the number of spiral turns decreases, which causes the spiral to expand (e.g., increasing the spiral radius); when the tube (365) is rotated with respect to the guide member (363) in the opposite direction, the number of spiral turns increases, which causes the spiral to shrink (e.g., decreasing the spiral radius).

In one embodiment of the present invention, the proximal end of the imaging assembly (the catheter assembly) contains a handle with markers (or indicators) that guide the operator in adjusting the spiral radius of the distal end and/or prevents/limits excessive expanding forces, rotations and/or displacements from being applied to the spiral of the imaging sheath, which may cause damage to the imaging assembly and/or the vessel wall. As a practical matter, observation of the images produced during a pull back of the imaging core provides a reliable means to ensure that the spiral is near enough to the vessel wall. If the imaging sheath is away from the vessel wall, the image produced will show the separation of the imaging sheath from the vessel wall. Anytime that the imaging sheath is too far from the vessel wall, the pull back may be discontinued, the spiral adjusted to produce the desired vessel wall contact/proximity and then the imaging pull back may be resumed.

FIG. 17 illustrates a cross section view along D-D' in FIG. 16. The tube (365) has a guide lumen (379) and an imaging lumen (373). The imaging lumen (379) connects to the imaging sheath to provide a continuous passageway for the optical fiber (377) for the control of the imaging core in the imaging sheath (361). The guide lumen (379) allows the guide member (363) to slide into the tube to compress the spiral length the imaging sheath or slide out of the tube to extend the spiral length of the imaging sheath. The cross-section of tube (365) may be oval or more egg-shaped and not circular, as shown, if desired.

Although FIGS. 16 and 17 illustrate the adjustment of the spiral length and the number of spiral turns through moving the tube, it is understood that it is the relative movement between the tube and the guide member that causes the adjustment of the spiral length and the number of spiral turns. The relative movement between the tube and the guide member can be achieved through fixing the tube to move the guide member (e.g., with respect to the vessel), or through fixing the guide member to move the tube (e.g., with respect to the vessel), or through moving both the guide member and the tube (e.g., with respect to the vessel) to cause the relative movement.

Further, in one embodiment, the imaging sheath is slidable within a lumen in the tube while the guide member is fixed relative to the tube to fix the spiral length. Advancing a length of imaging sheath through the lumen in the tube increases the length of the imaging sheath in the spiral for the given spiral pitch (e.g., at a given spiral length and a given number of spiral turns) and thus increases the spiral radius; withdrawing a length of imaging sheath reduces the spiral radius. In one embodiment, the guide member and the tube are fixed with respect to each other to have a fixed spiral length and/or a fixed number of spiral turns; sliding the imaging sheath into or out of the tube adjusts the length of the imaging sheath in the spiral to expand or collapse the spiral. In one embodiment, both the imaging sheath and the guide member are slidable in their respective lumens. A proximal handle/control mechanism can be used to control the spiral through controlling the relative positions of the imaging sheath, the guide member and/or the tube. The proximal relative longitudinal position of the guide member with respect to the tube can be controlled to adjust the spiral length; the proximal relative longitudinal position of the guide member and the imaging sheath can be controlled to adjust the spiral length; and the proximal relative rotation of the guide member with respect to the tube can be controlled to adjust the number of spiral turns. Selectively adjusting the length of the imaging sheath in the spiral, the spiral length and the number of spiral turns can expand or collapse the spiral, as discussed above. In some implementations, the imaging sheath is free to rotate at its proximal and/or distal end to relieve strains that may be introduced when the tube is rotated relative to the guide member.

Figure 18:
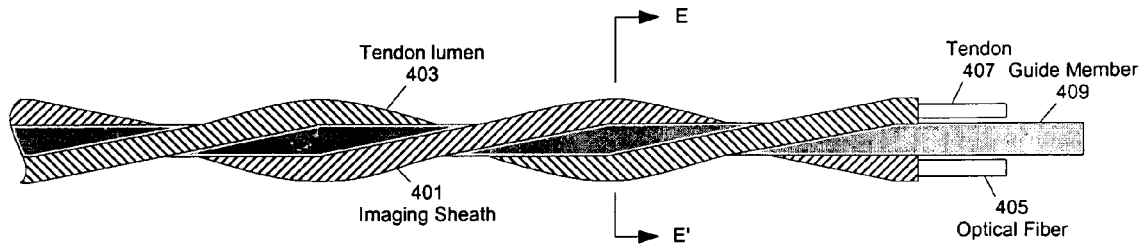
FIGS. 18-22 illustrate an imaging assembly with a tendon according to one embodiment of the present invention.
Figure 19:
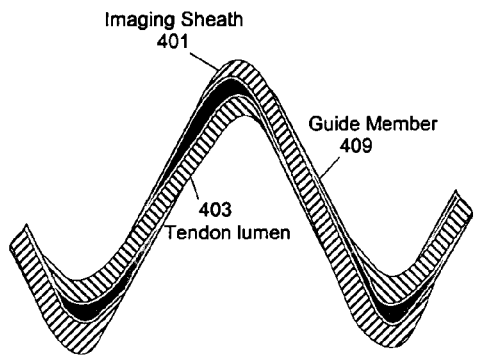
Figure 20:
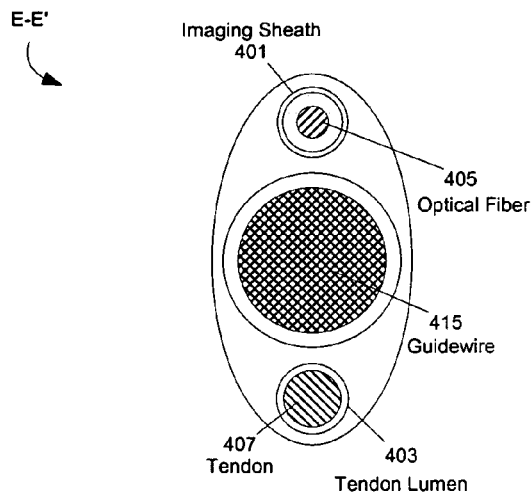

FIGS. 18-20 illustrate an imaging assembly on the distal end of a catheter (not shown) with a tendon according to one embodiment of the present invention. In FIG. 18, the tendon (407) is not in tension so that the guide member (409) is substantially straight. The tendon lumen (403) spirals around the guide member (409) on one side; and the imaging sheath (401) spirals around the guide member (409) on the opposite side of the tendon (407). The tendon (407) is preferably attached to the distal end of the tendon lumen (403) wall, but is otherwise free to move within the tendon lumen (403). The optical fiber (405), a portion of the imaging core, in the imaging sheath (401) provides the light passageway for OCT imaging and its proximal portion provides the control over the movement of the imaging core for scanning.

FIG. 19 shows the tendon bending the imaging assembly when the tendon is in tension (pulled proximal relative to the rest of the assembly). When the tendon is in tension, the guide member (409) and the imaging sheath (401) are bent into a spiral shape. The contraction force of the tendon causes the tendon lumen (403) to stay at the inside of the spiral; and the imaging sheath (401) is at the outside of the spiral. Thus, the tendon (407) and tendon lumen (403) are not in the way between the imaging sheath (401) and the spiral section of a vessel wall to be imaged.

FIG. 20 shows the cross section view along E-E' in FIG. 18. Although the cross-section is shown to be oval, it is to be understood that the cross-section could be constructed as circular or in other shapes. At least the outside facing portions of the imaging sheath (401) (e.g. the portion of the assembly that accommodates the imaging core) is transparent or adequately translucent so that the light can be projected from the imaging core to the vessel wall and scattered back to the imaging core through the imaging sheath (401). The imaging sheath (401) provides a passageway for the imaging core. The guidewire (415) is used to provide the stiffness to the assembly so that the distal portion of the imaging assembly is substantially straight when the tendon is not in tension. The guidewire may be slidable within a guidewire lumen of the guide member (409); alternatively, the guidewire may be integrated with the imaging sheath (401) and the tendon lumen (403). The imaging sheath (401) and the tendon lumen (403) are on the opposite sides of the guide member (409). When the tendon (407) is in tension, the tendon lumen (403) wall is compressed to reduce its length, which causes the bending of the assembly into a spiral.

The longitudinal translation of the tendon (407) relative to the tendon lumen (403) wall or the tension force applied to the tendon can be used to control the bending of the spiral. The greater the tension force or the proximal translation of the tendon (407) applied, the smaller the spiral pitch may be. The spiral of the tendon lumen (403) wall around the guide member (409) and the stiffness of the guide member (409) can be designed so that when the assembly is bent under tendon (407) control into a spiral, the spiral gently contacts the vessel wall without an excessive expanding force on the vessel wall. Note that only the imaging section of the catheter assembly is described here, as the distal tip and proximal sections of the catheter may be of conventional angioplasty and deflection catheter designs, respectively. As before, in some embodiments, the guidewire lumen can be eliminated, at least from the distal section of the catheter, when the catheter or imaging sheath is designed such that the imaging core and guidewire can replace each other within the imaging sheath.

Figure 21:
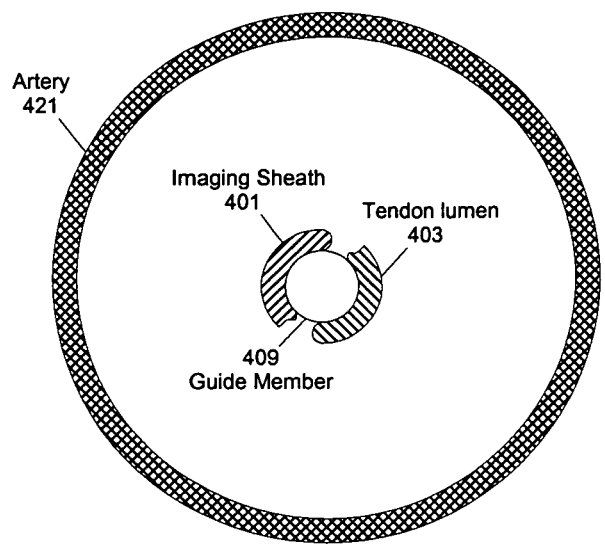

FIG. 21 shows an axial slice view of the imaging assembly when the tendon is not in tension. In FIG. 21, the guide member (409) is substantially straight (see also FIG. 18) when the tendon is not in tension. Since the imaging assembly has a small overall radius, there is a significant distance between the imaging sheath and the wall of the artery (421). The imaging sheath (401) and the tendon lumen (403) spiral around the guide member (409). The blood between the artery wall and the imaging sheath may reduce the imaging capability and the image quality of the OCT scan. In FIG. 21, only small length segments (the width of the view slice) of the imaging sheath (401) and the tendon lumen (403 wall) are shown so that both segments of them can be seen clearly.

Figure 22:
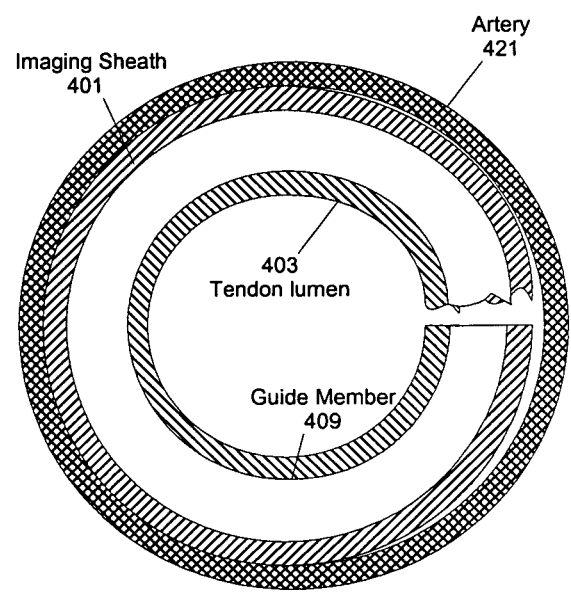

FIG. 22 shows an axial slice view of the imaging assembly when the tendon is in tension. In FIG. 22, the guide member (409) is bent into a spiral when the tendon is in tension (see also FIG. 19). The tendon lumen (403) is at the inside of the spiral; and the imaging sheath (401) is at the outside of the spiral, gently contacting the wall of the artery (421). Since the imaging assembly spirals into contact with the artery, the imaging sheath (401) is very close to a spiral section of the wall of the artery (421). The blood in the artery will not reduce the imaging capability and the image quality of the OCT scan of the spiral section of the artery wall. Also, the spiral-shaped imaging assembly does not severely block the blood flow in the artery.

The assembly of FIGS. 18-22 can be used for OCT imaging, where the imaging sheath (e.g., 401) can be used to accommodate the imaging core of an OCT imaging system. Similar assemblies can also be used for photodynamic therapy to the vessel wall and/or to perform the optical temperature measurement of the vessel wall. The assembly can be deformed into a spiral using the tendon (e.g., 407) to bring the sheath (e.g., 401) for the core of photodynamic therapy or optical temperature measurement into gentle contact, or closer to, a section of the vessel wall.

Figure 23:
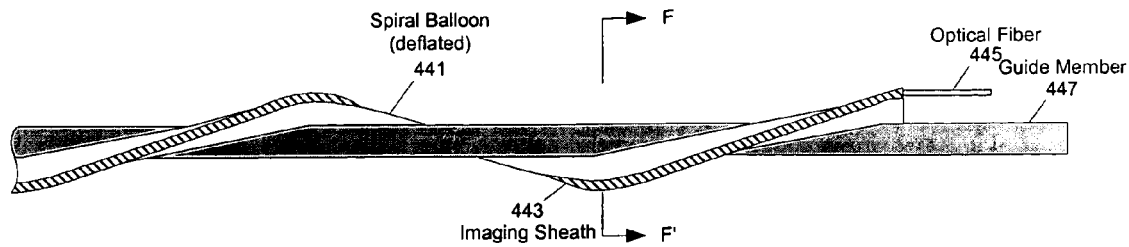
FIGS. 23-26 illustrate an imaging assembly with a spiral balloon according to one embodiment of the present invention.
Figure 24:
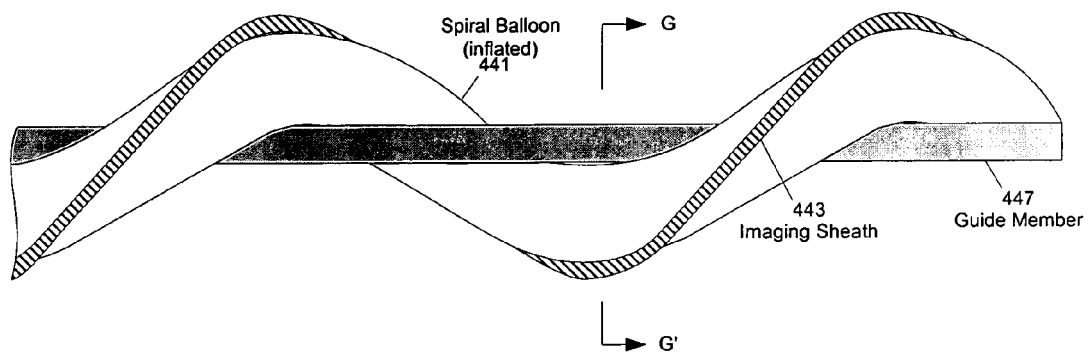

FIGS. 23-26 illustrate an imaging assembly with a spiral balloon according to one embodiment of the present invention. FIG. 23 illustrates a distal portion when the spiral balloon (441) is deflated; and FIG. 24 illustrates a distal portion when the spiral balloon (441) is inflated. The imaging sheath (443) spirals on the back of the spiral balloon (the outside of the spiral balloon). When the spiral balloon is deflated, the overall diameter of the distal portion is small, allowing the free movement of the distal portion in an internal channel. When the spiral balloon is inflated, the backside of the spiral balloon pushes the imaging sheath toward a spiral section of the internal channel. The guide member (447) has a stiffness to remain substantially straight before and after the spiral balloon is inflated but is flexible enough to traverse in the internal channel. Thus, even when the spiral balloon is inflated, the distal portion of the assembly leaves at least a spiral portion of the channel unblocked so that fluid (e.g., blood) can still flow in the channel.

Figure 25:
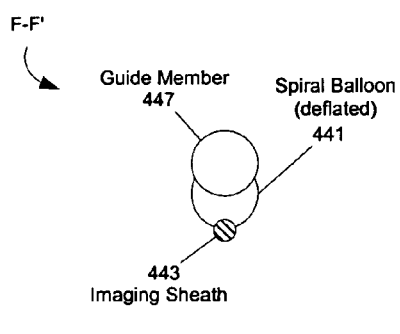
Figure 26:
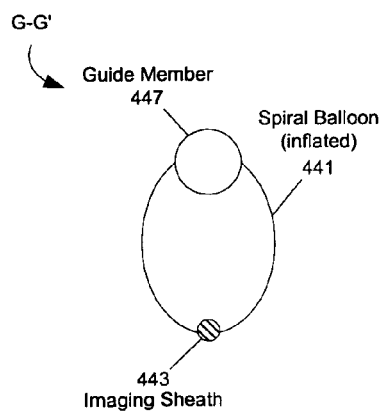

FIG. 25 illustrates a cross section view along F-F' in FIG. 23 where the spiral balloon is deflated. FIG. 26 illustrates a cross section view along G-G' in FIG. 24 where the spiral balloon is inflated. The guide member at or near in the center of the spiral regardless whether the spiral balloon is inflated or deflated. Thus, the imaging sheath is away from the wall of the internal channel (e.g., an artery) and close to the guide member when the balloon is deflated; and the imaging sheath is away from the guide member and close to (or gently touching) a spiral section of the wall when the balloon is inflated.

When the spiral balloon is inflated, the outside of the spiral balloon is stretched. In one embodiment, the imaging sheath is flexible and fixedly attached to the spiral balloon. Thus, when the spiral balloon is inflated, the imaging sheath is stretched together with the backside of the spiral balloon. Alternatively, the imaging sheath is movable relative to the imaging sheath. For example, the spiral balloon has a lumen housing the imaging sheath; the imaging sheath is slidable with respect to the spiral balloon in the lumen. Thus, when spiral balloon is inflated, the imaging sheath expands to have a spiral radius according to the backside of the spiral balloon and slides within the lumen to avoid being stretched. The distal end of the imaging sheath may be free to move; thus, when the spiral balloon is inflated, the distal end of the imaging sheath moves proximal to reduce the spiral length to avoid being stretched. Alternatively, the distal end of the imaging sheath may be fixed to the spiral balloon and the guide member; the proximal end of the imaging sheath is slidable with respect to a tube; thus, when the spiral balloon is inflated, a portion of the imaging sheath slides out of the tube to increase the length of the part of the imaging sheath that spirals on the back of the spiral balloon (due to the increase in spiral radius). In one embodiment, the balloon has a small attachment to the imaging sheath. Alternatively, the balloon may be attached to the sheath through a loop (not shown in FIGS. 25 and 26). Through such attachment arrangements, the sheath is prevented from being crushed/deformed when the balloon is inflated. Deforming the imaging sheath may make the movement of the imaging core within it difficult. Alternatively, the movement of the imaging sheath in radial and circumferential directions may be constrained to the spiral balloon along a number of points on the backside of the spiral balloon; and the imaging sheath is slidable along the spiral of the backside of the balloon.

Figure 27:
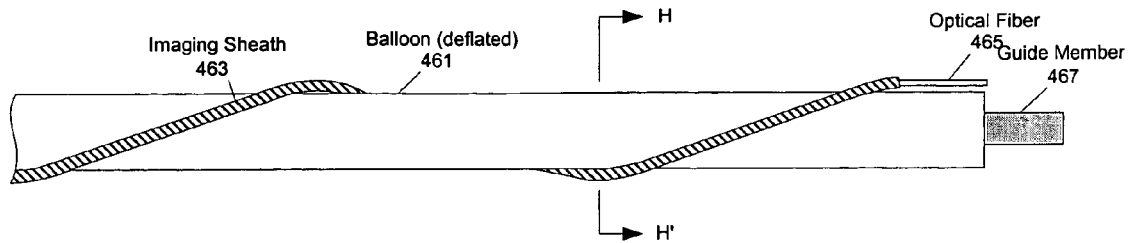
FIGS. 27-30 illustrate an imaging assembly with a regular balloon according to one embodiment of the present invention.
Figure 28:
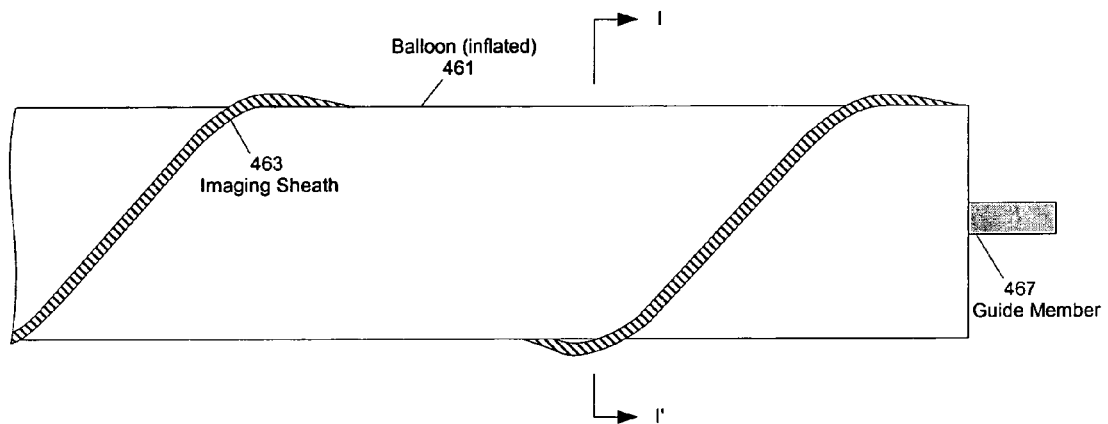

FIGS. 27-30 illustrate an imaging assembly with an elastic or compliant balloon according to one embodiment of the present invention. FIG. 27 illustrates a distal portion when the balloon (461) is deflated; and FIG. 28 illustrates a distal portion when the balloon (461) is inflated. The balloon (461) encloses a distal section of the guide member (467); and the imaging sheath (463) spirals outside the balloon. When the balloon is deflated, the overall diameter of the distal portion is reduced for positioning or repositioning the distal portion in an internal channel. When the balloon is inflated, the inflated balloon expands the spiral radius of imaging sheath so that the imaging sheath is close to or in contact with a spiral section of the internal channel. The guide member (467) has a stiffness to remain substantially straight but is flexible enough to traverse in the internal channel.

An elastic or compliant balloon may almost completely block the internal channel when the balloon is fully inflated. In one embodiment of the present invention, the guide member (467) includes a reperfusion catheter chassis. Although the elastic balloon causes more blockage of the blood flow in the vessel compared to a spiral balloon, the reperfusion lumen of the catheter chassis provides a channel for blood flow in the vessel. Alternatively, to avoid blockage of the flow in the channel (e.g., blood flow in the artery), the balloon may be inflated only to a degree such that the expanded spiral radius of the imaging sheath spiral is close to the radius of the channel; thus, the imaging sheath is close enough (e.g., within the imaging radius) to a spiral section of the wall; and the balloon would not completely block the internal channel. For example, the balloon may be inflated so that the spiral radius of the imaging sheath is still smaller than the radius of the internal channel. Thus, the flow may go through the spiral around the balloon and outside the imaging sheath.

Figure 29:
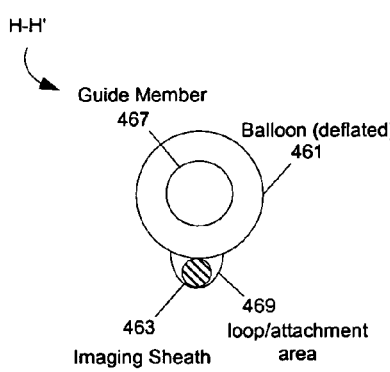
Figure 30:
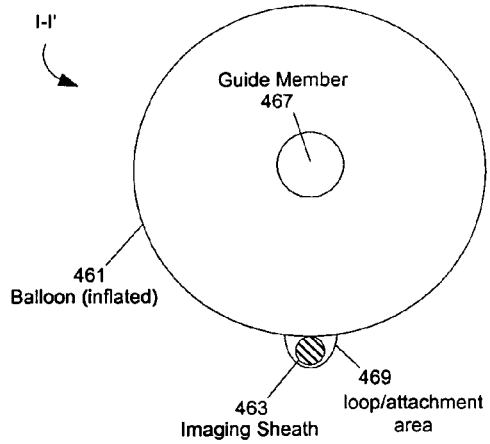

FIG. 29 illustrates a cross section view along H-H' in FIG. 27 where the balloon is deflated. FIG. 30 illustrates a cross section view along I-I' in FIG. 28 where the balloon is inflated. The guide member is at or near the center of the spiral of the imaging sheath. Thus, the imaging sheath shrinks toward the center to reduce the overall radius of the assembly when the balloon is deflated and expands to be substantially uniformly close a spiral section of the wall when the balloon is inflated. FIGS. 29 and 30 also illustrate a loop/attachment area (469) which constrains the imaging sheath (463) to the outer surface of the balloon (461). The loop/attachment area (469) does not constrain the imaging sheath (463) in the longitudinal direction so that, when the balloon is deflated or inflated, the imaging sheath is not compressed or stretched longitudinally. The loop/attachment area (469) can be applied only at several locations along the imaging sheath. The loop/attachment area can also extend in along the imaging sheath to define a lumen.

The imaging sheath may be flexible so that the imaging sheath stretches with the outside of the balloon when the balloon is inflated. Alternatively, the imaging sheath may be slidable with respect to the imaging sheath (e.g., in a lumen attached to the balloon or constrained along a spiral on the outside of the balloon). Alternatively, the imaging sheath is pre-formed with a small spiral radius so that the imaging sheath wraps around the balloon. When the balloon is inflated, the balloon temporarily expands the imaging sheath. When the balloon is deflated, the imaging sheath springs back to the small spiral radius to remain wrapped on the balloon.

In one embodiment of the present invention, when the balloon (441 or 461) is inflated or deflated, the spiral pitch for the imaging sheath remains substantially the same. When the spiral pitch is fixed, the length of the imaging sheath in the spiral changes as the spiral radius changes. In one embodiment, the imaging sheath is attached at or near the distal end of the balloon's major Outside Diameter (OD) and the imaging sheath is designed to accommodate the length changes caused by the balloon's inflation. In one implementation, the imaging sheath has one or more telescoping sections; loops, a channel, or segments of channels are used to loosely constrain the imaging sheath to the balloon; alternatively, the imaging sheath is fixedly attached to the balloon OD at one or more locations between telescoping sections of the imaging sheath. In one implementation, the imaging sheath is constrained along a spiral path outside balloon (e.g., using a number of loops, or a transparent/translucent channel, or a number of segments of channels); the imaging sheath is slidable along the spiral path to adjust the length of the imaging sheath in the spiral over the balloon. For example, when the balloon is inflated, a length of the imaging sheath is pulled into the spiral located outside the balloon by the balloon inflating force. When the balloon is deflated, the length of the imaging sheath can be withdrawn at the proximal end (or pushed out from the spiral by the deflating balloon) to wrap the imaging sheath tightly on the balloon. Alternatively, the imaging sheath is made of an elastic material, which can stretch and shrink back to conform to the OD of the balloon.

Figure 31:
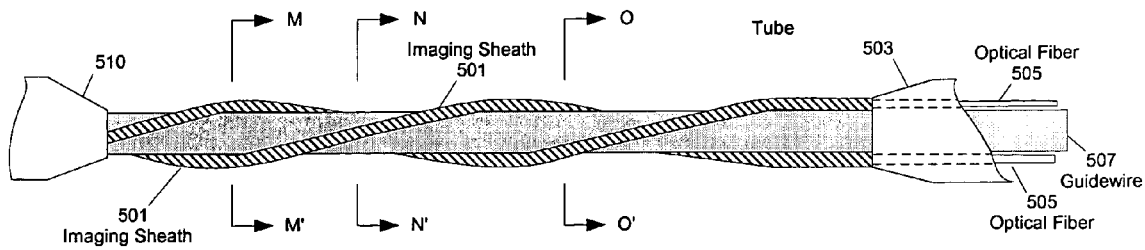

FIGS. 31-38 illustrate an imaging assembly with a plurality of imaging sheaths according to one embodiment of the present invention. In FIG. 31, a guidewire (507) is slidable and rotatable with respect to a tube (503). Two imaging sheaths spiral around the guidewire that extends outside the tube (503). The distal ends of the imaging sheath are fixed to the distal end (510) of the guidewire. The proximal ends of the imaging sheath are fixed to the tube (503). The tube contains lumens connected to the imaging sheath to provide continuous passageways for the optical fibers (505) of the OCT system.

When the guidewire (507) fully extends outside the tube, the spiral length of the imaging sheaths is stretched to fully reduce the spiral radius. Thus, the imaging sheaths (501) wrap around the guidewire (507) as illustrated in FIG. 31.

Figure 32:
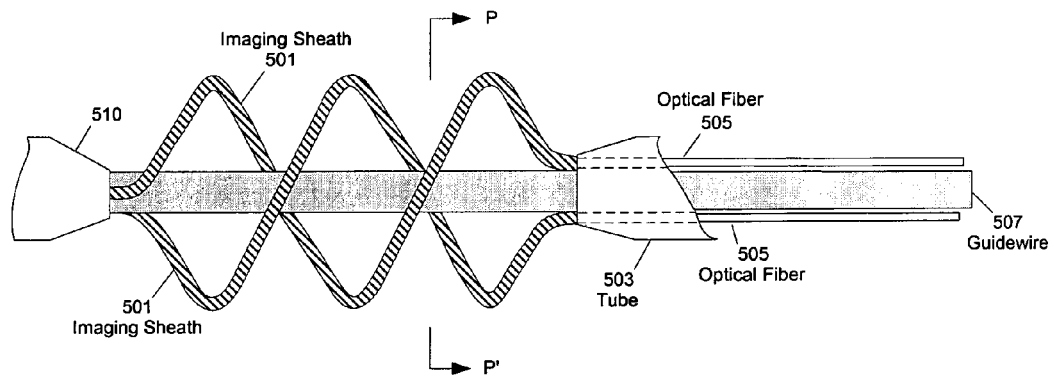
Figure 33:
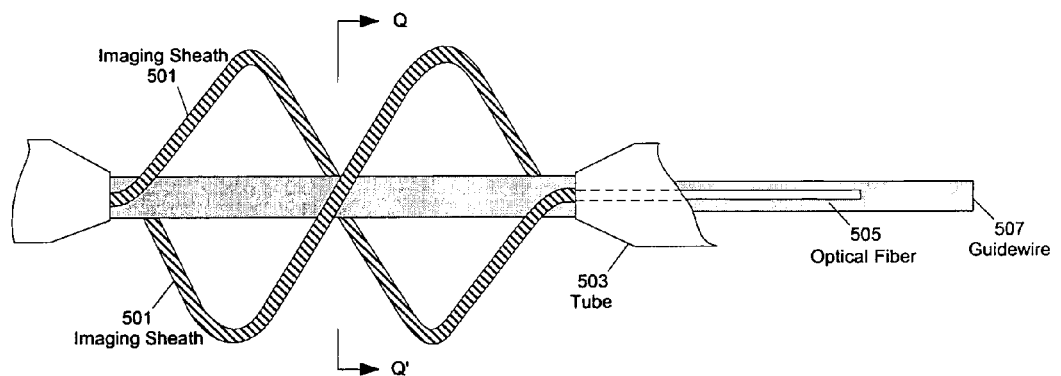

When the guidewire (507) slides into the tube, the spiral length of the imaging sheaths is shortened to increase the spiral radius. Thus, the spirals of the imaging sheaths (501) expand in radius, as illustrated in FIG. 32. Further, the guidewire can rotate with respect to the tube to change the number of spiral turns and thus the spiral radius. FIG. 33 illustrates the spirals with the reduced number of spiral turns and the increased spiral radius, after the tube (503) is rotated with respect to the guidewire (507) from the position in FIG. 32. In practice, the tube is typically not rotated with respect to the vessel; the guidewire is rotated with respect to the vessel so that the tube and the guidewire rotate with respect to each other. The relative rotation between the tube and the guidewire adjusts the number of spiral turns. Similarly, the relative longitudinal translation between the tube and the guidewire adjusts the spiral length. One may hold the tube still with respect to the vessel and move the guidewire with respect to the tube to adjust the spiral length and the number of spiral turns, or hold the guidewire still with respect to the vessel and move the tube with respect to the guidewire, or move both the guidewire and the tube with respect to the vessel to cause relative movement between the guidewire and the tube. Further, in one embodiment, the imaging sheaths can slide in the tube to adjust the length of imaging sheaths in the spirals (e.g., through advancing or withdrawing a length of the imaging sheaths into the tube while holding the guidewire and the tube still). Selectively adjusting the length of the imaging sheath in the spiral, the spiral length and the number of spiral turns can expand or collapse the spiral.

The example of FIGS. 31-33 illustrates an embodiment in which each imaging sheath houses its own imaging core and each of the imaging core has an optical fiber (505) attached and connected to the proximal end of the assembly. Each of the imaging cores can scan a spiral section of the wall close to the corresponding imaging sheath. Alternatively, a single imaging core may be inserted into one of the imaging sheath for scanning a spiral section of the wall close to the imaging sheath in which the imaging core is housed. Different spiral sections of the wall can be scanned through inserting into and sliding out from the imaging sheaths one after another.

The OCT images of the spiral sections of the wall can be combined to provide a more complete view of the wall. When the spiral sections overlap, a 360-degree of circumferential image of the wall can be constructed.

Although the example of FIGS. 31-38 illustrates only two imaging sheaths, from this description it will be apparent to one skilled in the art that a plurality of imaging sheaths (e.g., three or more) can be used in general. It will also be apparent to one skilled in the art that the embodiments described relative to FIGS. 15 through 17 and 23 through 30 may be similarly modified to contain multiple imaging sheaths.

FIGS. 34-36 illustrate cross section views along M-M', N-N' and O-O' in FIG. 31, where the guidewire fully extends outside the tube (503) to collapse the spirals of the imaging sheaths onto the guidewire (507). The spiral radius $d_1$ (511) is small in FIG. 35, since the imaging sheaths wrapping tightly around the guidewire (507). In the small radius configuration, the distal portion of the imaging assembly can be inserted into and moved along an internal channel (e.g., an artery) to reach a target location. FIGS. 34-36 show the different positions of the imaging sheaths (501) relative to the guidewire (507) at different cross sections according to the spirals.

FIG. 37 illustrates a cross section view along P-P' in FIG. 32, where the guidewire slides into the tube (503) to expand the spirals of the imaging sheaths. The spiral radius $d_2$ (513) is larger than $d_1$ (511) so that the imaging sheaths are close to the spiral sections of the wall of the internal channel.

FIG. 38 illustrates a cross section view along Q-Q' in FIG. 33, where the guidewire has been rotated to reduce the number of spiral turns of the imaging sheath and expand the spirals of the imaging sheaths. The spiral radius $d_3$ (515) is larger than $d_2$ (513) so that the imaging sheaths are moved closer to the wall of the internal channel (or to gently contact the wall).

FIGS. 39-42 illustrate an imaging assembly with a spiral balloon covering the imaging sheath according to one embodiment of the present invention. In FIG. 39, the spiral balloon is deflated so that the overall radius of the distal portion of the assembly is small. In FIG. 40, the spiral balloon is inflated. The imaging sheath spirals around the guide member (537) regardless whether the spiral balloon is inflated or not. When the spiral balloon is inflated, the balloon pushes the blood in the vessel out of the region between the spiral imaging sheath (531) and a spiral section of the vessel wall so that the flow of the blood in the vessel is mainly in the region outside the light path between the imaging sheath and the vessel wall. At least the portion of the spiral balloon between the vessel wall and the imaging sheath is transparent or adequately translucent. The spiral balloon allows blood flow even after the balloon is fully inflated. The spiral radius of the imaging sheath does not change. The inflated spiral balloon reduces the thickness of the layer of blood between the imaging sheath and the vessel wall to that smaller than the imaging depth so that the vessel wall can be clearly scan imaged.

FIG. 41 illustrates a cross section view along R-R' in FIG. 39. The spiral balloon (533) covers the imaging sheath (531). When the balloon is deflated, the overall radius of the distal portion is small so that the distal portion of the assembly can be moved to a target location in the blood vessel. In one embodiment, deflated balloons are folded (not shown in FIGS. 39 and 41). Thus, the balloon is not significantly stretched (a non-compliant balloon) or significantly stretched (a compliant balloon) when fully inflated as in FIGS. 40 and 42. Alternatively, elastic balloons that are fully elastic over the range of use can be used (as shown in FIGS. 39-42).

FIG. 42 illustrates a cross section view along S-S' in FIG. 40. The spiral balloon (533) expands to expel the blood from a region between the imaging sheath (531) and a spiral section of the vessel well to reduce or eliminate the blood effect. The spiral radius of the imaging sheath remains the same; and the shape and the position of the spiral of the imaging sheath relative to the guide member (537) is not changed.

In one embodiment, the imaging sheath is integrated with the guide member. After the imaging of a spiral section of the vessel wall, the spiral balloon is deflated; and the distal portion is repositioned for the imaging of a different spiral section of the vessel wall (e.g., for the same segment of the vessel or a different segment of the vessel). For example, the guide member may be moved along the vessel for a distance (e.g., a half or one third of the spiral pitch) for the imaging of a different spiral section; alternatively, the guide member may be rotated (e.g., for 60 or 90 degrees) for the imaging of a different spiral section. Alternatively, the guide member may include a guidewire and a lumen housing the guidewire. The imaging sheath is attached to guide member so that when the guide member rotates and/or slides with respect to the guidewire, the imaging sheath can be repositioned for the imaging of a different spiral section.

Figure 43:
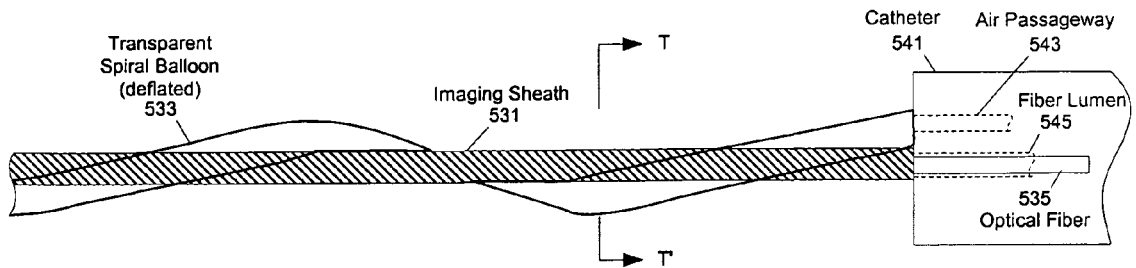
FIGS. 43-46 illustrate an imaging assembly with a straight imaging sheath enclosed in a spiral balloon according to one embodiment of the present invention.

FIGS. 43-46 illustrate an imaging assembly with a straight imaging sheath enclosed in a spiral balloon according to one embodiment of the present invention. In FIG. 43, a transparent or adequately translucent spiral balloon (533) covers a spiral portion of the imaging sheath (531). The spiral balloon spirals around the imaging sheath to cover a spiral portion of the imaging sheath. The imaging sheath and the spiral balloon are connected to the distal end of a catheter (541), which includes an air or fluid passageway (543) for inflating or deflating the balloon and a fiber lumen (545) as a passageway for the optical fiber (535) which is a part of the imaging core in the imaging sheath (531). In one embodiment, deflated balloons are folded (not shown in FIGS. 43 and 45). Thus, the balloon is not significantly stretched (a non-compliant balloon) or significantly stretched (a compliant balloon) when fully inflated as in FIGS. 44 and 46. Alternatively, elastic balloons that are fully elastic over the range of use can be used (as shown in FIGS. 43-46).

Figure 44:
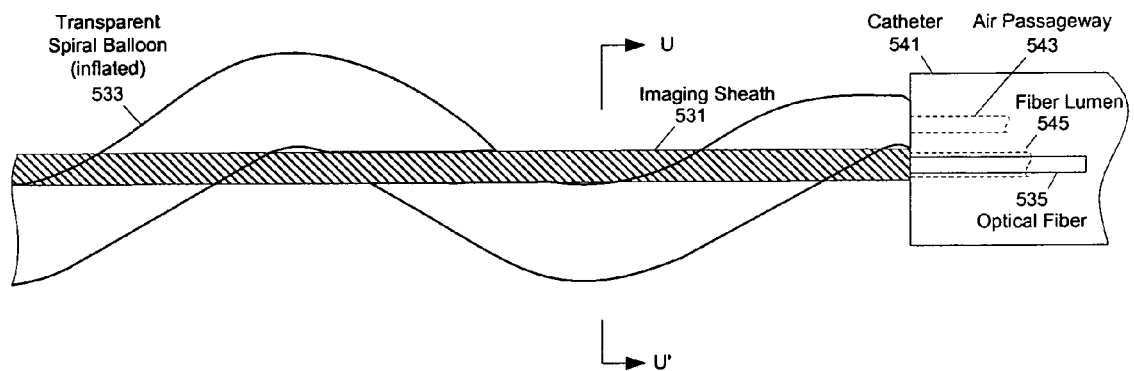

FIG. 44 shows the spiral balloon clearing a spiral region outside the imaging sheath to reduce or eliminate the blood effect for the OCT imaging of a spiral portion of the wall of the blood vessel. After the spiral balloon is inflated to gently contact or move closer to a spiral section of the vessel wall, the beam from the imaging core in the imaging sheath can be projected from within the balloon, through the balloon onto a spiral section of the vessel wall without having to pass a significant layer of blood. Thus, the blood effect on OCT imaging for the spiral section of vessel wall can be eliminated or reduced to acceptable levels.

Figure 45:
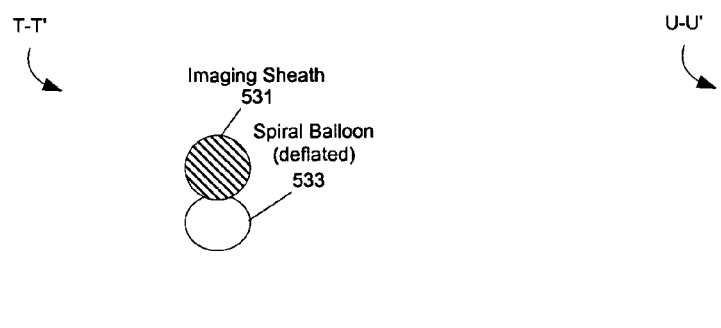

FIG. 45 illustrates a cross section view along T-T' in FIG. 43. The spiral balloon (533) covers a spiral section of the imaging sheath (531). When the balloon is deflated, the overall radius of the distal portion is small so that the distal portion can be positioned or repositioned in the blood vessel.

Figure 46:
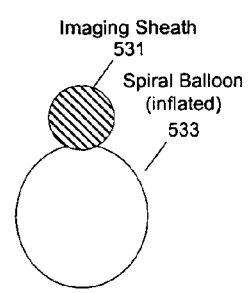

FIG. 46 illustrates a cross section view along U-U' in FIG. 44. The spiral balloon (533) expands to push the blood from a region between the imaging sheath (531) and a spiral section of the vessel well to reduce or eliminate the blood effect. The imaging sheath remains substantially straight when the spiral is inflated. The inflated spiral balloon occupies only a portion of the cross section of the vessel (e.g., a quarter to half of the cross section area of the vessel). Thus, the inflated spiral balloon does not block the blood flow in the vessel.

In one embodiment, the spiral balloon (533) is rotatable about and/or slidable along the imaging sheath (e.g., the spiral balloon is mounted on a transparent or adequately translucent tube which is outside the imaging sheath and movable with respect to the imaging sheath). Thus, after scanning a spiral section of the vessel wall, the spiral balloon can be deflated, repositioned with respect to the imaging sheath, and inflated again for the scanning of a different spiral section.

Figure 47:
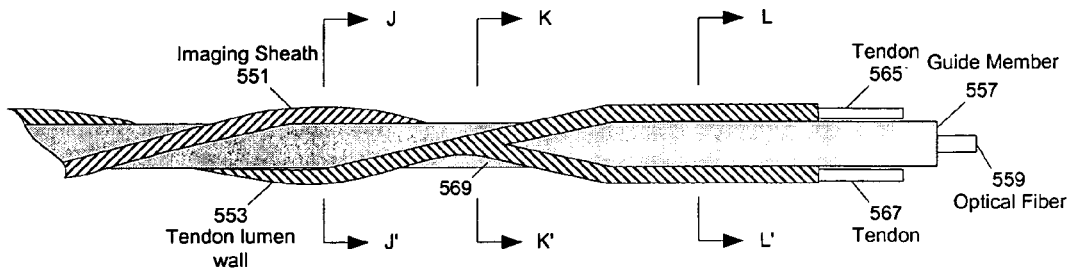
FIGS. 47-50 illustrate an imaging assembly with a plurality of tendons on a portion of the assembly to reduce bending according to one embodiment of the present invention.

FIGS. 47-50 illustrate an imaging assembly with a plurality of tendons on a portion of the assembly to reduce bending according to one embodiment of the present invention. FIG. 47 illustrates a transition section of the imaging assembly. The distal portion of the imaging assembly includes an imaging sheath (551) and a tendon lumen wall (553) spiraling on the opposite sides of a guide member (557). The tendon (565) is attached to the distal end of the imaging assembly or tendon lumen wall (553). When the tendon enclosed within the tendon lumen wall (553) is in tension, the tendon bends the distal portion into a spiral, as illustrated in FIGS. 18-20. However, in the proximal portion of the assembly, it is desirable to reduce the bending of the assembly so that the assembly remains substantially straight even when the tension force is applied to the tendon enclosed within the tendon lumen wall (553) of the distal portion; this proximal portion of the assembly bends according to the turns of the vessel, not the tension force applied to bend the distal portion of the assembly.

Figure 51:
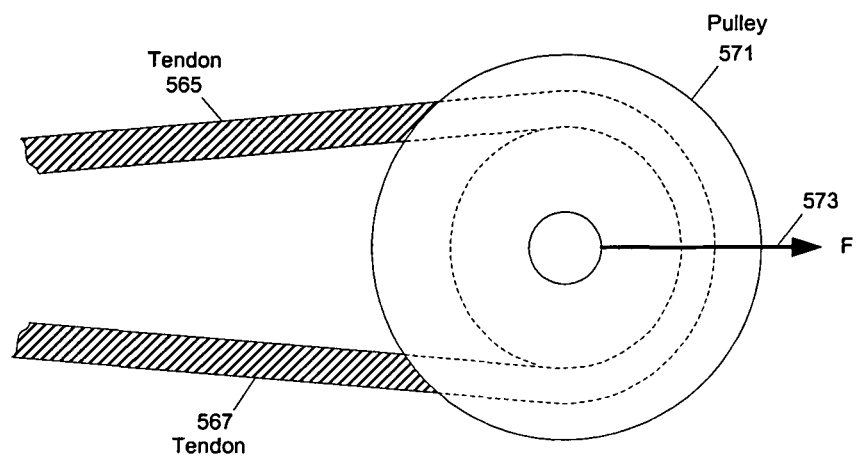
FIGS. 51-52 illustrate an assembly to balance the forces in two tendons for an imaging assembly according to one embodiment of the present invention.
Figure 52:
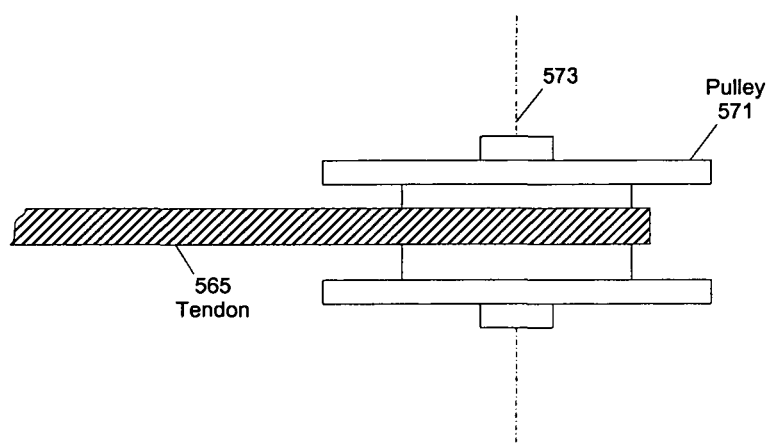

In one embodiment of the present invention, to reduce or eliminate the bending moment caused by the tension force, a transition portion (569) is used to connect a plurality of tendons to the tendon enclosed within the tendon lumen wall (553) of the distal portion. After the transition portion (e.g., near the cross section L-L'), the plurality of tendons are distributed around the outside of the assembly so that the resulting tension forces in the tendons cause a small or no net bending moment for the assembly. For example, when two tendons are used in the cross section L-L', the tendons (565 and 567) can be placed to balance the bending moments resulting from the tension forces and cause little or no bending moment at the cross section of the assembly. To apply equal forces on the tendons (565 and 567), a pulley as shown in FIGS. 51 and 52 can be used.

Although the example of FIGS. 47-50 shows the use of two tendons to reduce or eliminate the bending moment on a portion of the assembly, it is understood that a plurality of tendons can be distributed outside the assembly to reduce or eliminate the net bending moment produced by the tension forces. Further, the tendons may further merge to form a circular shell round the assembly.

Figure 48:
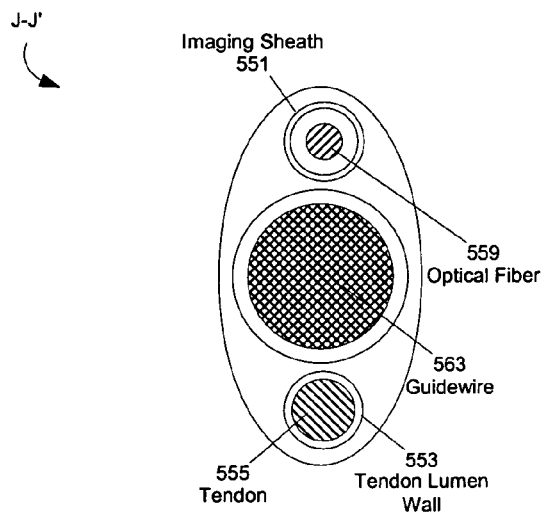

FIG. 48 shows a cross section view along J-J' in FIG. 47. Near the cross section along J-J' in FIG. 47, the tendon lumen wall (553) and imaging sheath (551) spiral around the guide member (557). The tendon lumen wall (553) is on the opposite side of the imaging sheath (551). When a tension force is applied on the tendon (555), the tension force of the tendon causes a bending moment to bend the distal portion of the assembly into a spiral.

Figure 49:
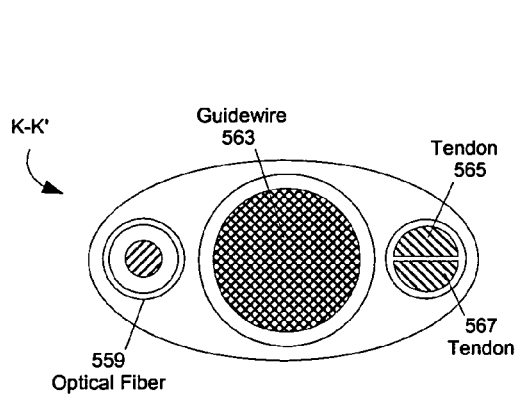

FIG. 49 shows a cross section view along K-K' in FIG. 47. Near the cross section along K-K' in FIG. 47, the tendon and the tendon lumen starts to split into two. For example, the tendon (555) in the portion near the cross section of J-J' splits into the two tendons (565 and 567). Each of the tendon (565 and 567) provides half of the tension force required by the tendon (555) in the distal portion of the assembly.

Between cross section K-K' and L-L', the tendons (565 and 567) are routed to positions to reduce or eliminate the overall bending moment caused by the tension force.

Figure 50:
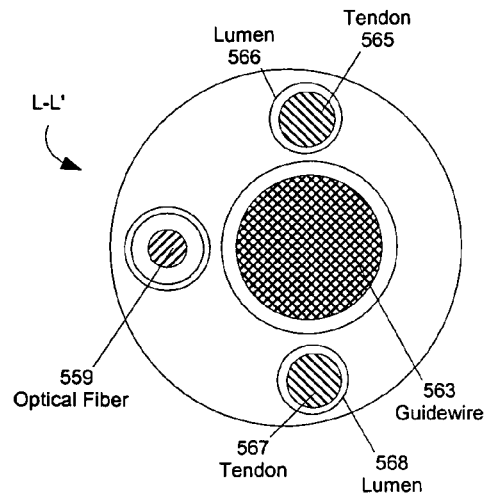

FIG. 50 shows a cross section view along L-L' in FIG. 47. Near the cross section along L-L' in FIG. 47, the tendons (565 and 567) are housed in separate lumens (566 and 568). The tendons (565 and 567) are arranged on the opposite sides of the geometric or bending center of this portion of the assembly so that when equal tension forces are applied on the tendons (565 and 567), the resulting net bending moment on the cross section is significantly reduced or completely eliminated.

Typically, the tension forces in the tendons are generated through pulling the tendons relative to the tendons' lumen walls. While the tendons are in tension, the tendons lumen walls and the part of the assembly that it is coupled to (e.g., fixedly attached to) are in compression. The resultant of the compression forces that counterbalance the tension forces in the tendons is typically centered at or near the geometric center of the cross section of the assembly (e.g., when a same type of material is used to form the tendon lumen walls in a symmetric design and the part of the assembly that is fixedly coupled to the tendon lumen walls). Thus, when the resultant of the tendon tension forces is also centered at the geometric center of the cross section of the assembly, there will be no net bending moment generated from pulling the tendons.

Thus, the distribution of the tendons on the rest of the assembly significantly reduces or completely eliminates the bending moment caused by the tension forces of the tendons. When the tendons at the proximal end of the assembly are pulled to put the tendon in the distal end in tension, which bends the distal portion of the assembly into a spiral, the rest of the assembly is still substantially straight.

FIGS. 51-52 illustrate an assembly to balance the forces in two tendons for an imaging assembly according to one embodiment of the present invention. FIG. 51 shows a side view of a pulley (571) used to balance the forces on the tendons (565 and 567) at the proximal end of an imaging assembly for bending a distal portion of the imaging assembly. When a force F (573) is applied on the axis of the pulley (571), the pulley (571) distributes equal tension forces on the tendons (565 and 567). FIG. 52 shows a top view of the pulley (571) balancing the forces for the tendons (565 and 567). The pulley (571) can rotate freely about the axis (573). When the forces applied on the tendons (565 and 567) are not equal, the unbalanced forces cause the pulley to rotate until the tension forces in the tendons are equal.

FIGS. 51-52 illustrate an example of using a pulley to directly balance the forces in the tendons. Alternatively, the forces in the tendons can be substantially balanced indirectly through the control of the amount of stretch in the tendons. For example, when the tendons have the same cross section area and the same length when not in tension, the same amount of stretch applied on the tendons generates the same amount of tension forces in the tendons. Thus, a device can be used at the proximal end of an imaging assembly to provide equal amount of stretch for each of the tendons to substantially balance the forces in the tendons and to reduce or eliminate the bending moment caused by the forces in the tendons.

Further details about a tendon deflection system with reduced bending moment can be found in a co-pending U.S. patent application Ser. No. 10/255,034, filed Sep. 25, 2002, which is incorporated here by reference.

Figure 53:
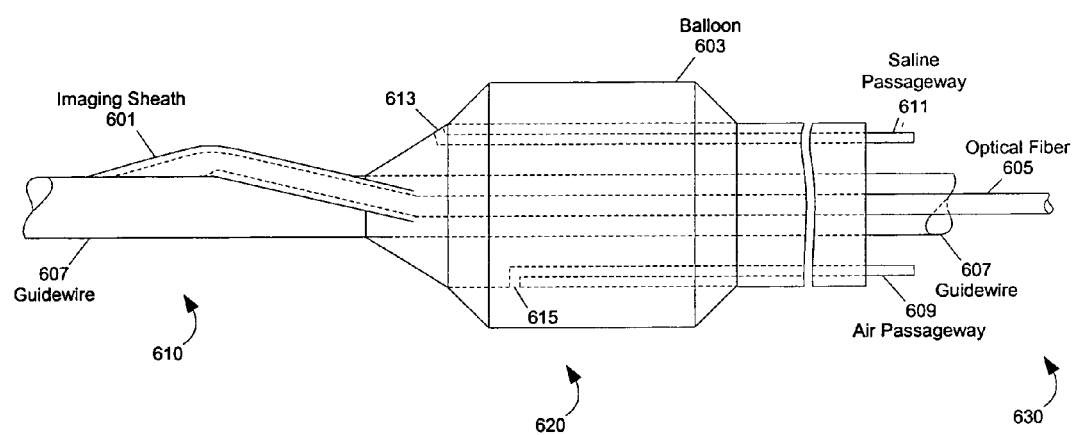
FIG. 53 illustrates a catheter assembly according to one embodiment of the present invention.

FIG. 53 illustrates a catheter assembly according to one embodiment of the present invention. The distal portion of the assembly (610) includes a guidewire (607) and an imaging sheath (601) spiraling around the guidewire (607). The imaging sheath (607) is attached to the guidewire (607) at the distal end, as illustrated in FIG. 15. Thus, when the guidewire is pulled, the spiral of the imaging sheath (601) is compressed in length and expanded in diameter, as illustrated in FIG. 16. When the guidewire extends out, the spiral of the imaging sheath collapse around the guidewire, as illustrated in FIG. 15.

A portion (620) that is close to the distal portion (610) may include a balloon (603). The balloon (603) may be inflated or deflated through an opening (615) to an air or fluid passageway 609. An opening (613) connected to the saline passageway (611) can be used to inject saline. This portion may further include one or more needles (not shown in FIG. 53) for delivering therapeutic substances to the blood vessel wall (e.g., according to the diagnosis based on the OCT imaging using the imaging sheath (601)). The balloon may be used to positioning the needle(s) for delivering therapeutic substances. After the imaging of the internal wall of an artery for the detection of a vulnerable plaque, the operator can push the guidewire so that the radius of the spiral of the imaging sheath shrinks and the imaging sheath wraps around the guidewire; then, the operator may advance this portion (620) to the location of the detected vulnerable plaque for treatment.

The proximal portion (630) is can be manipulated outside a body to operate the distal portion (601) that is inserted into the artery for OCT scanning. For example, the guidewire (607) at the proximal portion (630) can be pulled to cause the spiral of the imaging sheath at the distal portion to expand and gently contact the vessel wall; and the guidewire (607) can be pushed at the proximal portion (630) to cause the spiral of the imaging sheath at the distal portion to collapse for repositioning. The optical fiber (605) is connected to the imaging head in the imaging sheath through a passageway in the catheter and the imaging sheath. The optical fiber (605), which may be wrapped within a sleeve, can be pulled (or pushed) and rotated to perform OCT scan using the imaging head in the imaging sheath in the distal portion. Air or fluid can be applied at the air or fluid passageway (609) at the proximal portion to inflate the balloon (603); and, saline can be applied at the saline passageway to inject saline into the artery.

FIG. 53 illustrates a particular type of distal portion with a guidewire and a spiral imaging sheath. Other types of distal portions for an imaging assembly, such as those illustrated in FIGS. 6-46, can also be used. From this description, a person skilled in the art can envision various different combinations of different portions of the imaging assembly for OCT imaging and for therapeutic operations. Embodiments of the present invention are not limited to the particular combinations illustrated in the Figures.

From this description, it is understood that various assemblies according to embodiments of present invention, as illustrated in FIGS. 6-53 can be used for OCT imaging as well as photodynamic therapy to the vessel wall and/or to perform the optical temperature measurement of the vessel wall. The imaging sheath can be used to host the core for OCT imaging, for photodynamic therapy, and/or optical temperature measurement.

Figure 54:
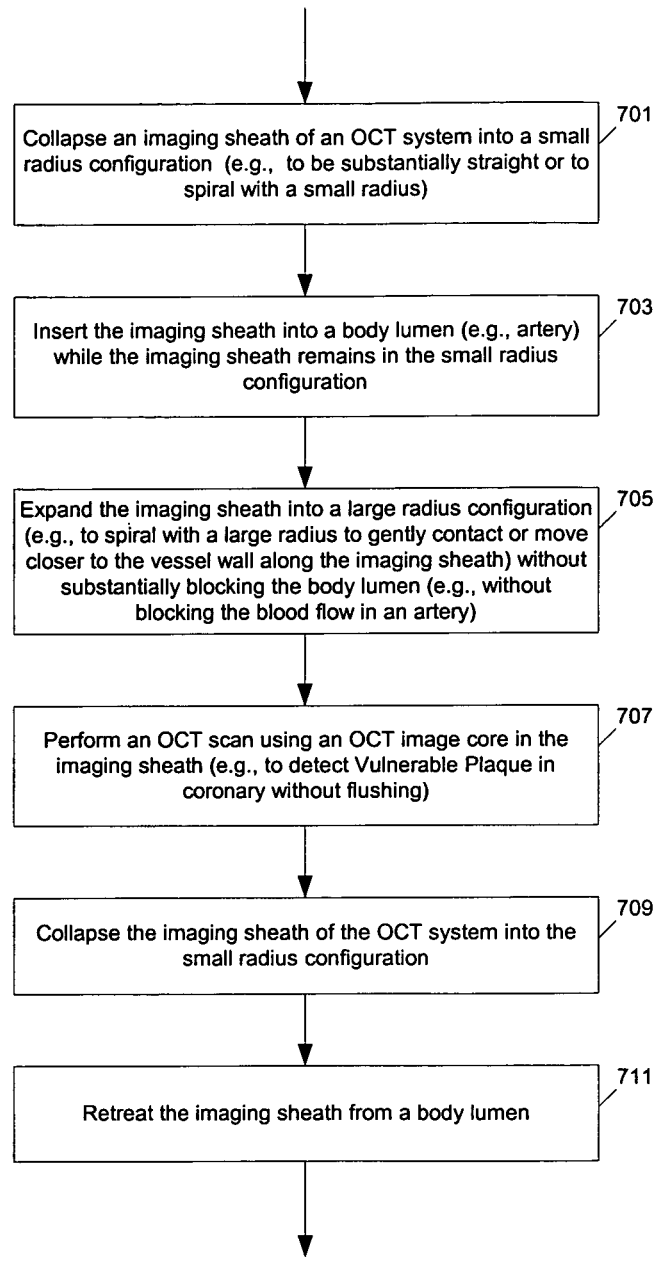
FIG. 54 illustrates a method of using an imaging assembly according to one embodiment of the present invention.

FIG. 54 illustrates a method of using an imaging assembly according to one embodiment of the present invention. After collapsing an imaging sheath of an OCT system into a small radius configuration (e.g., to be substantially straight or to spiral with a small radius) (701), an operator inserts the imaging sheath into a body lumen (e.g., artery) while the imaging sheath remains in the small radius configuration (703). For example, the operator may insert the straight guidewire into a spiral imaging sheath to straighten the imaging sheath as illustrated in FIG. 7, or pull the spiral guidewire out of the straight imaging sheath as illustrated in FIG. 10 or FIG. 13, or extend or push the guide member out of the tube to collapse the spiral imaging sheath around the guide member as illustrated in FIG. 15, or relax the tendon to substantially straighten the imaging sheath as illustrated in FIG. 18, or deflate the balloon in the distal portion as illustrated in FIG. 23, 27, 39 or 43. The portion of the imaging assemble being inserted into the body lumen is flexible enough to be able to follow the gentle turns of the body lumen without causing damage to the body lumen. The distal portion of the imaging assembly may have radiopaque markers (and/or OCT detectable features) so that the imaging sheath can be guided into a target location for OCT scanning.

After expanding the imaging sheath into a large radius configuration (e.g., to spiral with a large radius to gently contact or move closer to the vessel wall along the imaging sheath) without substantially blocking the body lumen (e.g., without blocking the blood flow in artery) (705), the operator performs an OCT scan using an OCT imaging core in the imaging sheath (e.g., to detect Vulnerable Plaque in coronary without flushing) (707). For example, the operator may pull the straight guidewire out of the spiral imaging sheath to cause the imaging sheath to spiral in the blood vessel as illustrated in FIG. 6, or insert a spiral guidewire to force the imaging sheath to spiral as illustrated in FIG. 9 or FIG. 12, or pull the guide member into the tube or rotate the guide member with respect to the tube to expand the imaging sheath spiral as illustrated in FIG. 16, or pull the tendon to bend the imaging sheath into a spiral as illustrated in FIG. 19, or inflate a balloon in the distal portion as illustrated in FIG. 24, 28, 40, or 44. In general, any OCT imaging techniques can be used with the present invention. Further, imaging techniques other than OCT may also be used with the present invention, especially those that may degrade in the imaging quality in the presence of a thick layer of blood between in the vessel and the imaging sheath. Further, the catheter system can also be used for optical temperature sensing through receiving lights at the core and/or for photodynamic therapy through delivering an optical beam from the core.

After collapsing the imaging sheath of the OCT system into the small radius configuration (709), the operator retreats the imaging sheath from a body lumen (711) or repositions it in the body lumen for further imaging. Alternatively, the operator may further advance a needle portion of the catheter assembly to provide treatments for a portion of the imaged section of the vessel wall according to the diagnosis based on the OCT imaging. The OCT imaging may also be used to guide the needle portion into a diseased portion of the vessel for treatment. Alternatively, the operator may reposition the imaging sheath for the scan of different portions of the vessel wall.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method to operate an assembly, the method comprising:
    selecting, based on a known radius of a blood vessel, the assembly having a pre-shaped spiral radius wherein a pitch length of spirals is less than ten times the radius of the vessel;

inserting a distal portion of the assembly into the blood vessel, the distal portion of the assembly having a sheath housing a core capable of at least one of: projecting a light onto a portion of the vessel and receiving a light from a portion of the vessel;

operating at a proximal portion of the assembly to expand the spiral radius having a plurality of spirals of the sheath in the vessel; and optically imaging the portion of the vessel with the core while the core moves through the spirals.

2. The method of claim 1, wherein said operating comprises:

moving a portion of a guidewire out of the distal portion of the assembly, the portion of the guidewire being substantially straight, the distal portion of the assembly being pre-shaped into spirals in absence of the portion of the guidewire.

3. The method of claim 2, further comprising:

inserting the portion of the guidewire into the distal portion of the assembly to temporarily straighten the distal portion; and repositioning the distal portion in the vessel while the guidewire is straightened.

4. The method of claim 2, further comprising:

moving the portion of the guidewire out of the distal portion of the assembly to allow the distal portion to recover back to a substantially straight shape; and repositioning the distal portion in the vessel while the guidewire is in the substantially straight shape.

5. A method of scanning a vessel wall of a blood vessel, comprising:

selecting, based on a known radius of the blood vessel, an assembly having a pre-shaped spiral radius wherein a pitch length of spirals is less than ten times the radius of the vessel;

slidably displacing a core in a longitudinally extending spiral pattern having a plurality of spirals within an inner surface of the vessel wall, the core being capable of at least one of projecting and receiving light; and optically imaging the portion of the vessel with the core while the core moves through the spirals.

6. The method of claim 5, further comprising:

imaging the inner surface of the vessel wall for the presence of a diseased region;

wherein the core is slidable along a spiral member having an orthogonal distance between adjacent spiral loops which is shorter than a minimum length of diseased regions to be detected plus two times an effective imaging depth of the core.

7. A method of scanning a vessel wall of a blood vessel, comprising:

selecting, based on a known radius of the blood vessel, an assembly having a pre-shaped spiral radius wherein a pitch length of spirals is less than ten times the radius of the vessel;

slidably displacing a core in a longitudinally extending spiral pattern of a sheath having a plurality of spirals within an inner surface of the vessel wall, the core being capable of at least one of projecting and receiving light; and imaging the inner surface of the vessel wall for the presence of a diseased region while the core slides along the spiral pattern.

* * * * *